US012728282B2

(12) United States Patent
Damato et al.

(10) Patent No.: US 12,728,282 B2
(45) Date of Patent: Sep. 8, 2026

(54) SYSTEMS AND METHODS FOR HIGH DOSE RATE BRACHYTHERAPY TREATMENT PLANNING USING CONSTRAINT OPTIMIZATION

(71) Applicants: MEMORIAL SLOAN-KETTERING CANCER CENTER, New York, NY (US); MEMORIAL HOSPITAL FOR CANCER AND ALLIED DISEASES, New York, NY (US); SLOAN-KETTERING INSTITUTE FOR CANCER RESEARCH, New York, NY (US)

(72) Inventors: Antonio Damato, White Plains, NY (US); Joel Beaudry, New York, NY (US); Gil'ad Cohen, Tenafly, NJ (US)

(73) Assignees: Memorial Sloan-Kettering Cancer Center, New York, NY (US); Memorial Hospital for Cancer and Allied Diseases, New York, NY (US); Sloan-Kettering Institute for Cancer Research, New York, NY (US)

( * ) Notice: Subject to any disclaimer, the term of this patent is extended or adjusted under 35 U.S.C. 154(b) by 45 days.

(21) Appl. No.: 18/857,413

(22) PCT Filed: Apr. 17, 2023

(86) PCT No.: PCT/US2023/018869
§ 371 (c)(1),
(2) Date: Oct. 16, 2024

(87) PCT Pub. No.: WO2023/205100
PCT Pub. Date: Oct. 26, 2023

(65) Prior Publication Data

US 2025/0262457 A1 Aug. 21, 2025

Related U.S. Application Data

(60) Provisional application No. 63/332,171, filed on Apr. 18, 2022.

(51) Int. Cl.
*A61N 5/10* (2006.01)

(52) U.S. Cl.
CPC ......... *A61N 5/1001* (2013.01); *A61N 5/1031* (2013.01)

(58) Field of Classification Search
None
See application file for complete search history.

(56) References Cited

U.S. PATENT DOCUMENTS

2005/0111621 A1 5/2005 Riker et al.
2015/0174431 A1* 6/2015 Bharat ................ A61N 5/1001 600/7

(Continued)

FOREIGN PATENT DOCUMENTS

WO WO-2020/218967 A1 10/2020
WO WO-2022/187378 A1 9/2022

OTHER PUBLICATIONS

Supplementary European Search Report 23792391.7 dated Feb. 16, 2026 (9 pages).

(Continued)

*Primary Examiner* — Marcus H Taningco
(74) *Attorney, Agent, or Firm* — Foley & Lardner LLP

(57) ABSTRACT

Systems and methods for HDR brachytherapy planning can include obtaining patient specific data of a patient, and determining, using the patient specific data, an optimization problem to solve for a single-fraction HDR monotherapy plan including an objective function to be optimized subject to one or more first constraints on radiation doses within one or more OAR regions and a second constraint on radiation (Continued)

doses within the PTV. The systems and methods can include optimizing the objective function subject to the one or more first constraints and the second constraint, determining whether the first single-fraction HDR monotherapy plan satisfies the first and second constraints, updating a bound value of the second constraint based on whether the first single-fraction HDR monotherapy plan satisfies the first and second constraints, and optimizing the objective function subject to the one or more first constraints and the second constraint with the updated bound value.

20 Claims, 14 Drawing Sheets

(56) References Cited

U.S. PATENT DOCUMENTS

2015/0258349 A1 9/2015 Grodski et al.
2017/0014642 A1* 1/2017 An .................... A61N 5/1084
2017/0165500 A1 6/2017 Flynn et al.
2020/0298019 A1 9/2020 Isola et al.
2021/0101023 A1 4/2021 Abel et al.
2021/0138264 A1 5/2021 Isola et al.
2021/0228907 A1* 7/2021 Olcott .................. A61N 5/1001
2021/0252307 A1* 8/2021 Kontaxis .............. A61N 5/1047
2023/0141197 A1* 5/2023 Andersson ........... A61N 5/1038
600/1

OTHER PUBLICATIONS

International Search Report and Written Opinion for PCT/US23/18869 dated Jul. 18, 2023, 9 pages.

* cited by examiner

SYSTEMS AND METHODS FOR HIGH DOSE RATE BRACHYTHERAPY TREATMENT PLANNING USING CONSTRAINT OPTIMIZATION

CROSS-REFERENCES TO RELATED APPLICATIONS

This application is the U.S. National Stage Application of International Application No. PCT/US2023/018869, filed Apr. 17, 2023, which claims the benefit of, and priority to, U.S. Provisional Application No. 63/332,171 filed on Apr. 18, 2022, each of which is incorporated herein by reference in its entirety.

FIELD OF THE DISCLOSURE

The present application relates generally to systems and methods for artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the present application relates to constraint optimization problem solving. In particular, the present application relates to high dose rate (HDR) Brachytherapy planning using constraint optimization. Specifically, systems and methods described herein allow for optimizing HDR Brachytherapy plans by enforcing hard constraints within organs-at-risk (OARs) while maximizing the radiation dose to the cancer site, e.g., prostate.

BACKGROUND OF THE DISCLOSURE

Brachytherapy is a form of internal radiation therapy usually used to treat prostate cancer. Compared to external radiotherapy where a machine outside the body is used to direct radiation beams to a tumor, brachytherapy involves placing or implanting radioactive sources or seeds in an anatomical region including the cancer site, e.g., prostate gland, leading to localized radiation. The radiation is significantly confined to the cancer site with reduced radiation exposure to the surrounding healthy tissues or organs. As such, the radiation from the radioactive seeds can kill the cancer cells while causing less damage to healthy tissues or organs compared to external radiotherapy techniques.

Brachytherapy can be administered either by permanently implanting low dose-rate (LDR) radioactive seeds or by temporarily placing high dose-rate (HDR) radioactive seeds. In the case of HDR brachytherapy, the radioactive seeds are placed within the anatomical region for predefined time period(s), e.g., few minutes, to deliver a high dose of radiation after which the seeds are removed. The radioactive seeds can be placed in the anatomical region hosting the tumor using hollow needles. One advantage of HDR brachytherapy is that there is no residual radiation in the patient after the treatment procedure. Given its localized radiation, brachytherapy is usually used for low-risk and/or intermediate-risk prostate cancers that have not spread beyond the prostate. However in some cases, it can be used for more aggressive cancers by combining it with external beam radiation or hormonal therapy.

SUMMARY

According to at least one aspect, a method for high-dose-rate (HDR) brachytherapy planning can include one or more processors obtaining patient specific data of a patient. The patient specific data includes information of an anatomical region of the patient having a planning target volume (PTV) and one or more organ-at-risk (OAR) regions, and indications of a plurality of clinical goals. The method can include the one or more processors determining, using the patient specific data, an optimization problem to solve for a single-fraction HDR monotherapy plan. The optimization problem includes an objective function to be optimized subject to one or more first constraints on radiation doses within the one or more OAR regions and a second constraint on radiation doses within the PTV. The method can include the one or more processors optimizing the objective function subject to the one or more first constraints and the second constraint, and determining whether the first single-fraction HDR monotherapy plan satisfies the one or more first constraints and the second constraint. The method can include the one or more processors updating a bound value of the second constraint based on whether the first single-fraction HDR monotherapy plan satisfies the one or more first constraints and the second constraint, and optimizing the objective function subject to the one or more first constraints and the second constraint with the updated bound value.

In some implementations, updating the bound value of the second constraint can includes decreasing the bound value of the second constraint upon determining that first single-fraction HDR monotherapy plan does not satisfy the one or more first constraints or the second constraint, and increasing the bound value of the second constraint upon determining that first single-fraction HDR monotherapy plan satisfies the one or more first constraints or the second constraint.

In some implementations, the method can include iteratively repeating the (i) determining whether the first single-fraction HDR monotherapy plan satisfies the one or more first constraints and the second constraint, (ii) updating of the bound value of the second constraint and (iii) optimizing the objective function subject to the one or more first constraints and the second constraint with the updated bound value until one or more stopping criteria are met. Iteratively optimizing the objective function subject to the one or more first constraints and the second constraint with the updated bound value can includes, at each iteration, identifying voxels in the PTV having radiation doses below a predefined radiation dose value, determining, for each identified voxel in the PTV, a corresponding radiation dose difference between the predefined radiation dose and the radiation dose at the identified voxel, and minimizing a sum of corresponding radiation dose differences of the identified voxels in the PTV subject to the one or more first constraints and the second constraint with the updated bound value.

In some implementations, optimizing the objective function subject to the one or more first constraints and the second constraint can include using linear programming. In some implementations, optimizing the objective function subject to the one or more first constraints and the second constraint can include solving for dwell time durations for a plurality of dwell positions. The optimization problem can further include a constraint on dwell time durations for neighboring dwell positions. In some implementations, the PTV includes a prostate region of the patient.

In some implementations, the method can include the one or more processors determining a region around the PTV, wherein the optimization problem further includes a third constraint on radiation doses within the region around the PTV, and optimizing the objective function subject to the one or more first constraints, the second constraint and the third constraint. In some implementations, the method can include identifying, for each OAR region, a sub-region of the OAR region expected to have highest radiation doses in the OAR region, and optimizing the objective function subject to the one or more first constraints applied to radiation doses within the sub-regions of the OAR regions.

In some implementations, the method can include the one or more processors generating, using the patient specific data, a three-dimensional (3D) structure representing an anatomical region of the patient, downsampling the 3D structure, and optimizing the objective function within the downsampled 3D structure.

According to at least one other aspect, a system for high-dose-rate (HDR) brachytherapy planning can include one or more processors and a memory storing computer instructions. The computer instructions when executed by the one or more processors cause the one or more processors to obtain patient specific data of a patient including information of an anatomical region of the patient having a planning target volume (PTV) and one or more organ-at-risk (OAR) regions, and indications of a plurality of clinical goals, and determine, using the patient specific data, an optimization problem to solve for a single-fraction HDR monotherapy plan. The optimization problem can include an objective function to be optimized subject to one or more first constraints on radiation doses within the one or more OAR regions and a second constraint on radiation doses within the PTV. The one or more processors can optimize the objective function subject to the one or more first constraints and the second constraint, and determine whether the first single-fraction HDR monotherapy plan satisfies the one or more first constraints and the second constraint. The one or more processors can update a bound value of the second constraint based on whether the first single-fraction HDR monotherapy plan satisfies the one or more first constraints and the second constraint, and optimize the objective function subject to the one or more first constraints and the second constraint with the updated bound value.

In some implementations, in updating the bound value of the second constraint the one or more processors can decrease the bound value of the second constraint upon determining that first single-fraction HDR monotherapy plan does not satisfy the one or more first constraints or the second constraint, and increase the bound value of the second constraint upon determining that first single-fraction HDR monotherapy plan satisfies the one or more first constraints or the second constraint.

In some implementations, the one or more processors can iteratively (i) determine whether the first single-fraction HDR monotherapy plan satisfies the one or more first constraints and the second constraint, (ii) update of the bound value of the second constraint and (iii) optimize the objective function subject to the one or more first constraints and the second constraint with the updated bound value until one or more stopping criteria are met. To iteratively optimize the objective function subject to the one or more first constraints and the second constraint with the updated bound value the one or more processors can, at each iteration, identify voxels in the PTV having radiation doses below a predefined radiation dose value, determine, for each identified voxel in the PTV, a corresponding radiation dose difference between the predefined radiation dose and the radiation dose at the identified voxel, and minimize a sum of corresponding radiation dose differences of the identified voxels in the PTV subject to the one or more first constraints and the second constraint with the updated bound value.

In some implementations, the one or more processors can optimize the objective function subject to the one or more first constraints and the second constraint using linear programming. In some implementations, to optimize the objective function subject to the one or more first constraints and the second constraint, the one or more processors can solve for dwell time durations for a plurality of dwell positions, and wherein the optimization problem further includes a constraint on dwell time durations for neighboring dwell positions. In some implementations, the one or more processors can determine a region around the PTV, wherein the optimization problem further includes a third constraint on radiation doses within the region around the PTV, and optimize the objective function subject to the one or more first constraints, the second constraint and the third constraint.

In some implementations, the one or more processors can identify, for each OAR region, a sub-region of the OAR region expected to have highest radiation doses in the OAR region, and optimize the objective function subject to the one or more first constraints applied to radiation doses within the sub-regions of the OAR regions. In some implementations, the one or more processors can generate, using the patient specific data, a three-dimensional (3D) structure representing an anatomical region of the patient, downsample the 3D structure, and optimize the objective function within the downsampled 3D structure.

According to at least one other aspect, a non-transitory computer-readable medium can store computer instructions, the computer instructions when executed by one or more processors cause the one or more processors to obtain patient specific data of a patient including information of an anatomical region of the patient having a planning target volume (PTV) and one or more organ-at-risk (OAR) regions, and indications of a plurality of clinical goals, and determine, using the patient specific data, an optimization problem to solve for a single-fraction HDR monotherapy plan. The optimization problem can include an objective function to be optimized subject to one or more first constraints on radiation doses within the one or more OAR regions and a second constraint on radiation doses within the PTV. The one or more processors can optimize the objective function subject to the one or more first constraints and the second constraint, and determine whether the first single-fraction HDR monotherapy plan satisfies the one or more first constraints and the second constraint. The one or more processors can update a bound value of the second constraint based on whether the first single-fraction HDR monotherapy plan satisfies the one or more first constraints and the second constraint, and optimize the objective function subject to the one or more first constraints and the second constraint with the updated bound value.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

Figure 1:
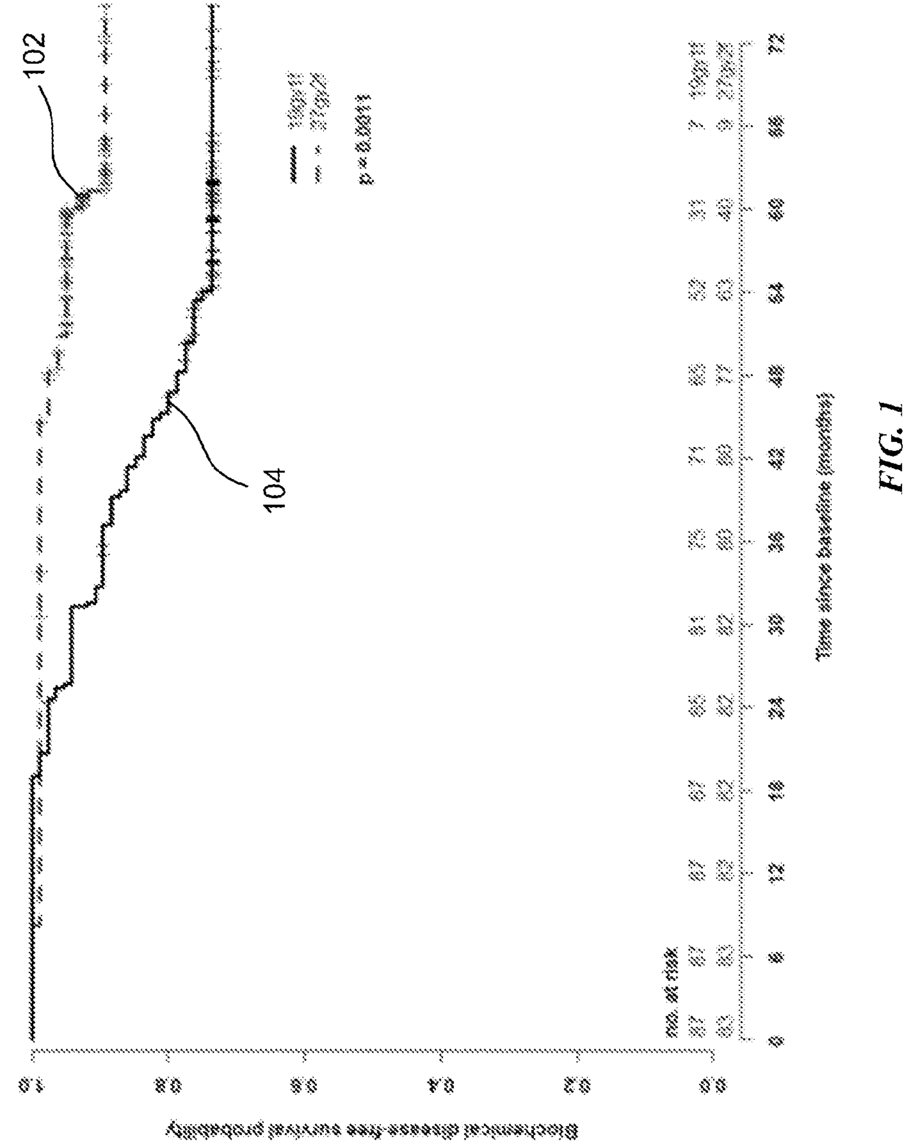
FIG. 1 shows plots illustrating experimental results for single-fraction HDR prostate monotherapy.

Following below are more detailed descriptions of various concepts related to, and embodiments of, systems and methods for brachytherapy planning. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Brachytherapy is a treatment option for clinically localized prostate cancer among many other treatment options. Brachytherapy involves placing a radioactive seed within an anatomical region of a patient to radiate the anatomical region and kill tumors therein. There are two forms or modes of brachytherapy, namely low-dose-rate (LDR) brachytherapy and high-dose-rate (HDR) brachytherapy. In LDR brachytherapy, a permanent LDR seed implant is placed in the patient's body at a target anatomical region, e.g., prostate, whereas HDR brachytherapy delivers a highly localized radiation dose to the tumor by placing a HDR radioactive seed at different locations of the target anatomical region for relatively short time durations.

HDR brachytherapy offers various advantages relative to LDR brachytherapy including flexibility in customizing treatment plans, reduced period of admission to hospitals as inpatient, reduced cost and uniformly accurate, precise, and reproducible dosimetry. For instance, LDR brachytherapy is typically characterized with dosimetric uncertainties due to post implant volume changes triggered by needle trauma and subsequent edema during the overall treatment period of several months. HDR brachytherapy avoids the dosimetric uncertainties by significantly reducing the time during which needles are inserted into the patient's body. Also, HDR brachytherapy allows for modulating and accurately controlling both the spatial seed position and the dwell time during treatment leading to improved radiation dose distribution.

Despite the above listed advantages, HDR brachytherapy is typically used in combination with or to boost external beam radiation therapy (EBRT). The combination of HDR brachytherapy and EBRT makes the treatment period relatively long with typically multiple hospital visits and a plurality of radiation sessions. Also, the HDR brachytherapy planning process typically leads to treatment plans that may not conform with dosimetry constraints within organs at risk (OARs). The non-conformity calls for human interference to adjust the treatment plan and makes the planning process longer, more complicated and more tedious.

It is desired to use HDR brachytherapy as a monotherapy treatment. As used herein, monotherapy means a therapy that use a single type of treatment. Also, even as a monotherapy treatment, another goal is to achieve a single-fraction monotherapy treatment where a patient undergoes a single HDR brachytherapy radiation session. In terms of HDR brachytherapy treatment planning, for monotherapy plans to be used as single-fraction monotherapy plans, generated plans are expected to have a high degree of conformity and dose escalation. In other words, a generated HDR brachytherapy plan is expected to exhibit high radiation dose with the target region, e.g., prostate, and high conformity within OARs to be used as a single-fraction monotherapy plan.

Referring now to FIG. 1, plots depicting experimental results for double-fraction and single-fraction HDR prostate monotherapy are shown. The x-axis in FIG. 1 represents the time passed since the last fraction and the y-axis represents the biochemical disease-free survival probability. The plot 102 represents the survival probability over time for patients who received two fractions of 13.5 Gy, and plot 104 represents the survival probability over time for patients who received a single fraction of 139 Gy. The single-fraction and double-fraction brachytherapy plans were developed using exiting brachytherapy planning techniques or optimizations. The single-fraction treatment plan was developed with the goal or hypothesizes to better target the intra-prostatic lesion (DIL) and to apply dose escalation in the prostate subject to the OAR constraints.

The results in FIG. 1 and plot 104 in particular show that biochemical failure is more likely to occur with patients who received the high-dose single fraction. Specifically, the survival probability starts to decrease significantly in the case of a single-fraction monotherapy plan starting from month 24 and goes down to about 0.7 after 54 months. The double-fraction monotherapy plan provides better performance with relatively higher survival probability.

In the current disclosure, novel brachytherapy planning methods and systems provide reliable single-fraction monotherapy plans with a high degree of conformity and dose escalation. According to at least one aspect, a HDR brachytherapy planning problem can be defined as an objective function to be optimized subject to one or more first constraints on radiation doses within one or more OAR regions and a second constraint on radiation doses within a target region, e.g., a prostate region. The first constraint(s) and the second constraint can be formulated or defined as hard constraints to be strictly satisfied. One or more processors can iteratively optimize the objective function or a related function subject to determine a treatment plan that strictly satisfies the one or more first constraints. The optimization involves escalating the radiation dose within the target region by adjusting or updating the second constraint at each iteration where a plan satisfying the first constraint(s) is found. The determined plan is a single-fraction monotherapy plan that satisfies the dosimetry constraints within the OARs. As discussed in further detail with regard to Table 1 below, the single-fraction monotherapy plans generated using the methods described herein are more efficient than EBRT treatment plans.

A. Computing and Network Environment

Figure 2A:
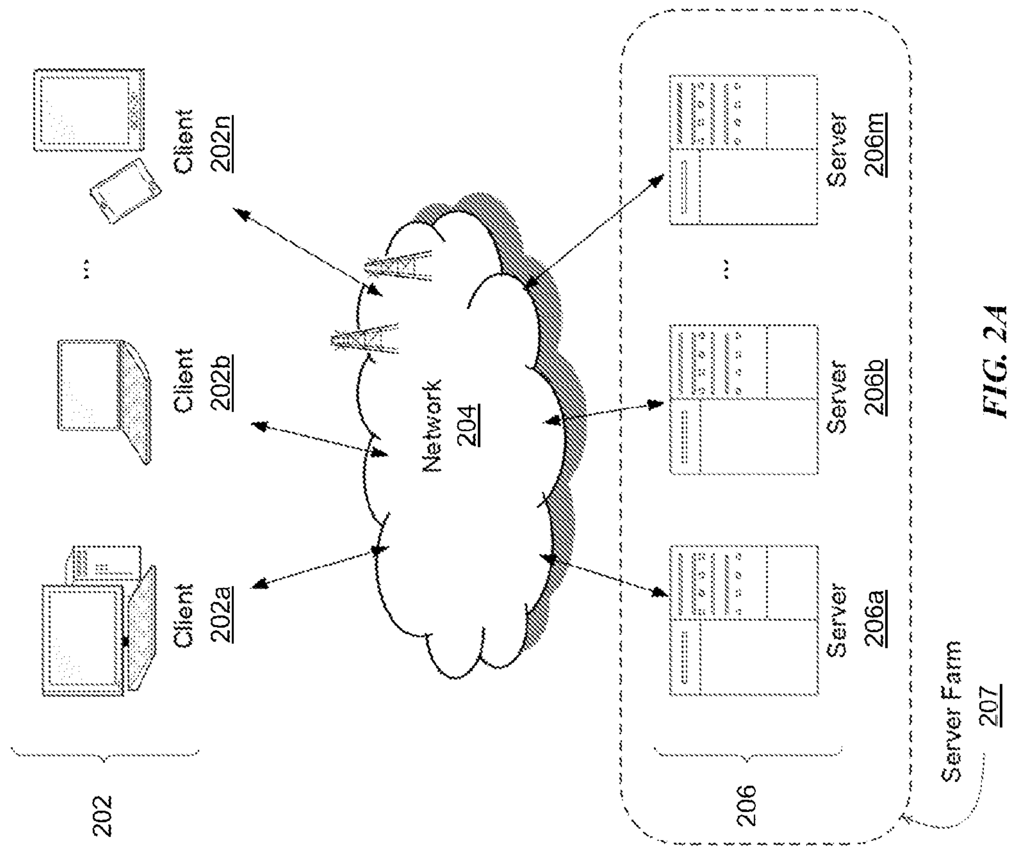
FIG. 2A is a block diagram depicting an embodiment of a network environment comprising client devices in communication with server devices in connection with the methods and systems described herein.

It may be helpful to describe aspects of the operating environment as well as associated system components (e.g., hardware elements) in connection with the methods and systems described herein. The methods described herein, such as methods 400 and 500, can be implemented or executed by any of the devices, or any combination thereof, described in relation to FIGS. 2A-2D. Referring to FIG. 2A, an embodiment of a network environment is depicted. In brief overview, the illustrated exploring network environment includes one or more clients 202*a*-202*n* (also generally referred to as local machine(s) 202, client(s) 202, client node(s) 202, client machine(s) 202, client computer(s) 202, client device(s) 202, endpoint(s) 202, or endpoint node(s) 202) in communication with one or more servers 206*a*-206*m* (also generally referred to as server(s) 206, node 206, or remote machine(s) 206) via one or more networks 204. In some embodiments, a client 202 has the capacity to function as both a client node seeking access to resources provided by a server and as a server providing access to hosted resources for other clients 202*a*-202*n*.

Although FIG. 2A shows a network 204 between the clients 202 and the servers 206, the clients 202 and the servers 206 may be on the same network 204. In some embodiments, there are multiple networks 204 between the clients 202 and the servers 206. In one of these embodiments, a network 904' (not shown) may be a private network and a network 904 may be a public network. In another of these embodiments, a network 904 may be a private network and a network 904' a public network. In still another of these embodiments, networks 904 and 904' may both be private networks.

The network 204 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 204 may be any type and/or form of network. The geographical scope of the network 204 may vary widely and the network 204 can be a body area network (BAN), a personal area network (PAN), a local-area network (LAN), e.g. Intranet, a metropolitan area network (MAN), a wide area network (WAN), or the Internet. The topology of the network 904 may be of any form and may include, e.g., any of the following: point-to-point, bus, star, ring, mesh, or tree. The network 204 may be an overlay network, which is virtual and sits on top of one or more layers of other networks 204'. The network 204 may be of any such network topology as known to those ordinarily skilled in the art capable of supporting the operations described herein. The network 204 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 204 may be a type of a broadcast network, a telecommunications network, a data communication network, or a computer network.

In some embodiments, the system may include multiple, logically-grouped servers 206. In one of these embodiments, the logical group of servers may be referred to as a server farm 207 or a machine farm 207. In another of these embodiments, the servers 206 may be geographically dispersed. In other embodiments, a machine farm 207 may be administered as a single entity. In still other embodiments, the machine farm 207 includes a plurality of machine farms. The servers 206 within each machine farm 207 can be heterogeneous—one or more of the servers 206 or machines 206 can operate according to one type of operating system platform (e.g., WINDOWS NT, manufactured by Microsoft Corp. of Redmond, Washington), while one or more of the other servers 206 can operate on according to another type of operating system platform (e.g., Unix, Linux, or Mac OS X).

In one embodiment, servers 206 in the machine farm 207 may be stored in high-density rack systems, along with associated storage systems, and located in an enterprise data center. In this embodiment, consolidating the servers 206 in this way may improve system manageability, data security, the physical security of the system, and system performance by locating servers 206 and high performance storage systems on localized high performance networks. Centralizing the servers 206 and storage systems and coupling them with advanced system management tools allows more efficient use of server resources.

The servers 206 of each machine farm 207 do not need to be physically proximate to another server 206 in the same machine farm 207. Thus, the group of servers 206 logically grouped as a machine farm 207 may be interconnected using a wide-area network (WAN) connection or a metropolitan-area network (MAN) connection. For example, a machine farm 207 may include servers 206 physically located in different continents or different regions of a continent, country, state, city, campus, or room. Data transmission speeds between servers 206 in the machine farm 907 can be increased if the servers 206 are connected using a local-area network (LAN) connection or some form of direct connection. Additionally, a heterogeneous machine farm 207 may include one or more servers 206 operating according to a type of operating system, while one or more other servers 206 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 207 may be de-centralized. For example, one or more servers 206 may comprise components, subsystems and modules to support one or more management services for the machine farm 207. In one of these embodiments, one or more servers 206 provide functionality for management of dynamic data, including techniques for handling failover, data replication, and increasing the robustness of the machine farm 207. Each server 206 may communicate with a persistent store and, in some embodiments, with a dynamic store.

Server 206 may be a file server, application server, web server, proxy server, appliance, network appliance, gateway, gateway server, virtualization server, deployment server, SSL VPN server, or firewall. In one embodiment, the server 206 may be referred to as a remote machine or a node. In another embodiment, a plurality of nodes may be in the path between any two communicating servers.

Figure 2B:
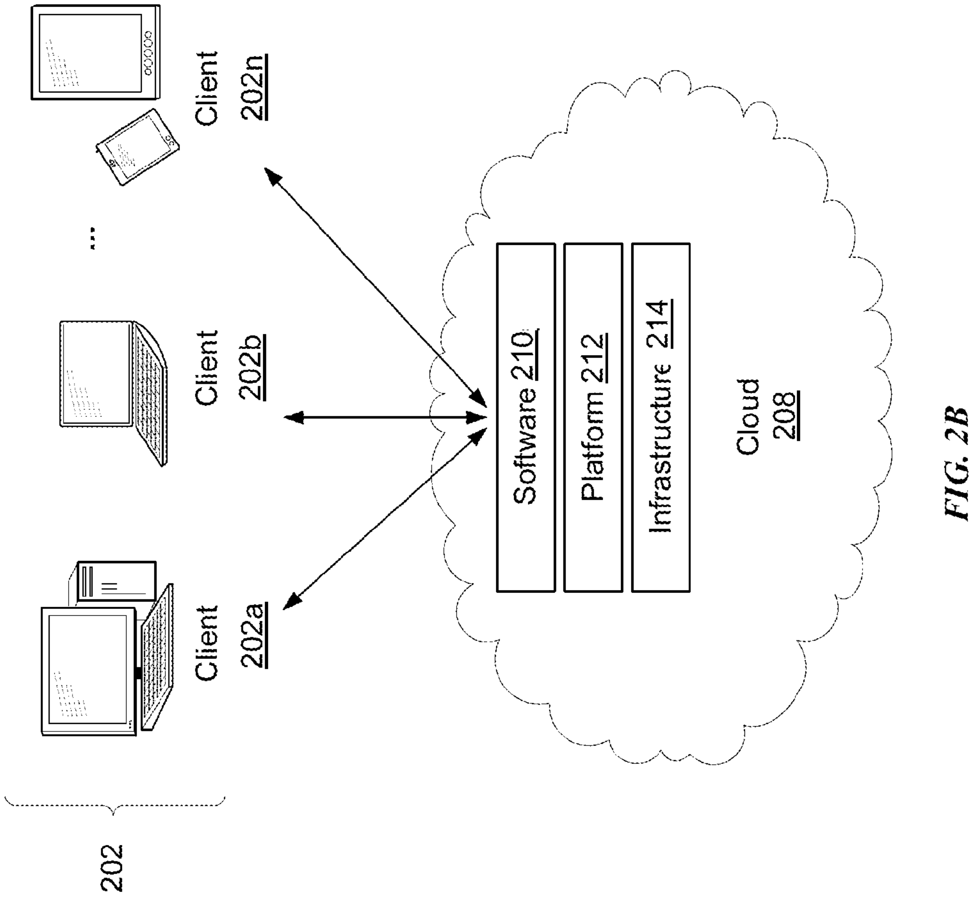
FIG. 2B is a block diagram depicting a cloud computing environment comprising client devices in communication with a cloud service provider in connection with the methods and systems described herein.

Referring to FIG. 2B, a cloud computing environment is depicted. A cloud computing environment may provide client 202 with one or more resources provided by a network environment. The cloud computing environment may include one or more clients 202*a*-202*n*, in communication with the cloud 208 over one or more networks 204. Clients 202 may include, e.g., thick clients, thin clients, and zero clients. A thick client may provide at least some functionality even when disconnected from the cloud 208 or servers 206. A thin client or a zero client may depend on the connection to the cloud 208 or server 206 to provide functionality. A zero client may depend on the cloud 208 or other networks 204 or servers 206 to retrieve operating system data for the client device. The cloud 208 may include back end platforms, e.g., servers 206, storage, server farms or data centers.

The cloud 208 may be public, private, or hybrid. Public clouds may include public servers 206 that are maintained by third parties to the clients 202 or the owners of the clients. The servers 206 may be located off-site in remote geographical locations as disclosed above or otherwise. Public clouds may be connected to the servers 206 over a public network. Private clouds may include private servers 206 that are physically maintained by clients 202 or owners of clients. Private clouds may be connected to the servers 206 over a private network 204. Hybrid clouds 208 may include both the private and public networks 204 and servers 206.

The cloud 208 may also include a cloud based delivery, e.g. Software as a Service (SaaS) 210, Platform as a Service (PaaS) 212, and Infrastructure as a Service (IaaS) 214. IaaS may refer to a user renting the use of infrastructure resources that are needed during a specified time period. IaaS providers may offer storage, networking, servers or virtualization resources from large pools, allowing the users to quickly scale up by accessing more resources as needed. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California. SaaS providers may offer the resources that PaaS provides, including storage, networking, servers, virtualization, operating system, middleware, or runtime resources. In some embodiments, SaaS providers may offer additional resources including, e.g., data and application resources.

Clients 202 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 202 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 202 may access SaaS resources through the use of web-based user interfaces, provided by a web browser. Clients 202 may also access SaaS resources through smartphone or tablet applications, including. Clients 202 may also access SaaS resources through the client operating system.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 2C:
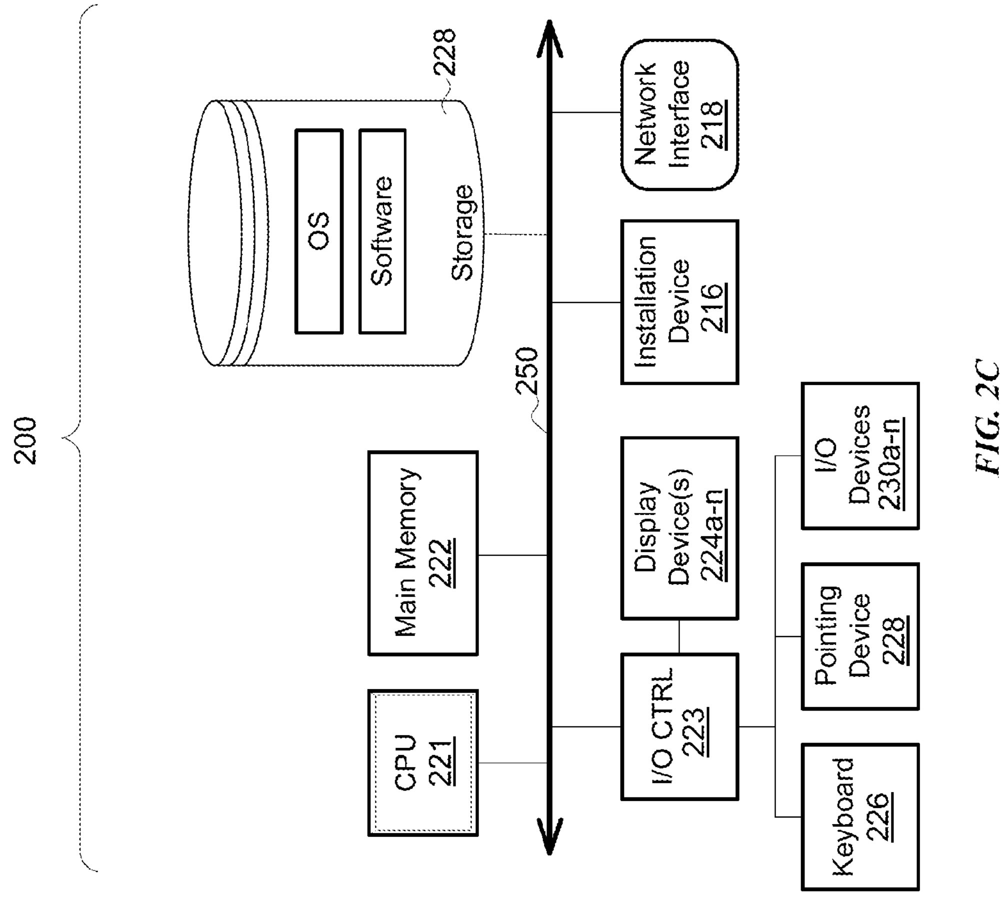
FIGS. 2C and 2D are block diagrams depicting embodiments of computing devices useful in connection with the methods and systems described herein.
Figure 2D:
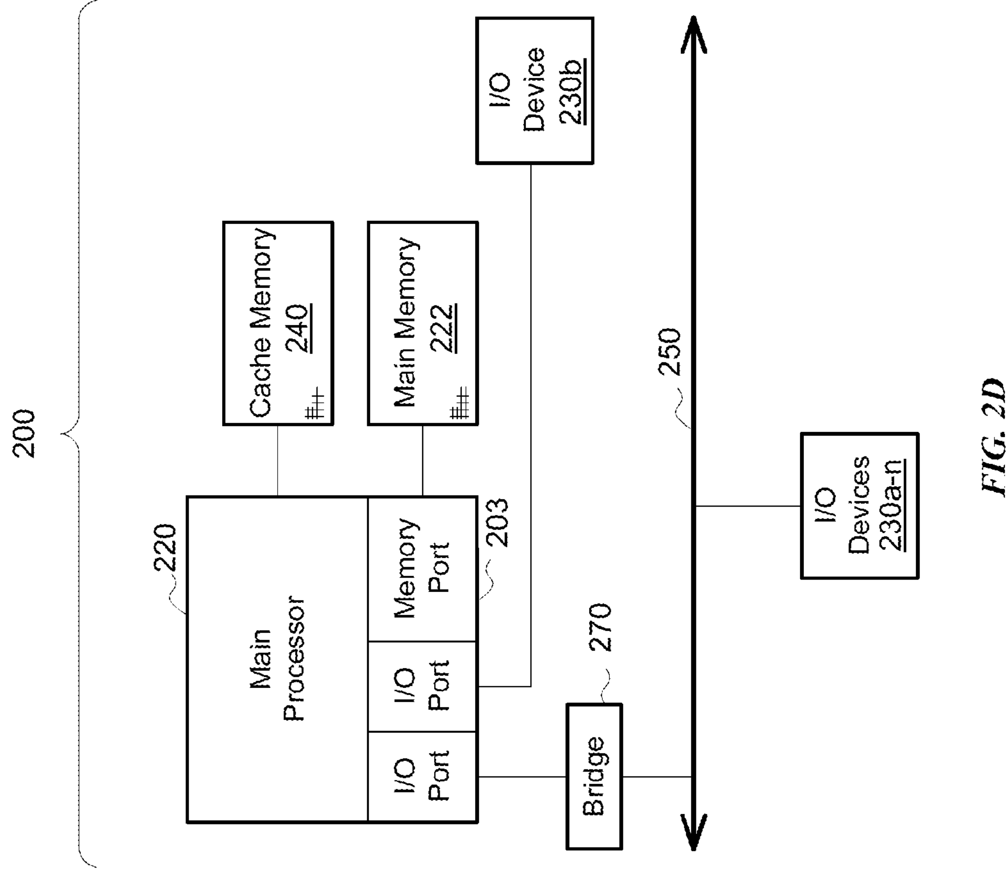

The client 202 and server 206 may be deployed as and/or executed on any type and form of computing device, e.g. a computer, network device or appliance capable of communicating on any type and form of network and performing the operations described herein. FIGS. 2C and 2D depict block diagrams of a computing device 200 useful for practicing an embodiment of the client 202 or a server 206. As shown in FIGS. 2C and 2D, each computing device 200 includes a central processing unit 221, and a main memory unit 222. As shown in FIG. 2C, a computing device 200 may include a storage device 228, an installation device 216, a network interface 218, an I/O controller 223, display devices 224*a*-224*n*, a keyboard 926 and a pointing device 227, e.g. a mouse. The storage device 228 may include, without limitation, an operating system, and/or software 220. As shown in FIG. 2D, each computing device 200 may also include additional optional elements, e.g. a memory port 203, a bridge 270, one or more input/output devices 930*a*-930*n* (generally referred to using reference numeral 230), and a cache memory 240 in communication with the central processing unit 221.

The central processing unit 221 is any logic circuitry that responds to and processes instructions fetched from the main memory unit 222. In many embodiments, the central processing unit 221 is provided by a microprocessor unit. The computing device 200 may be based on any of these processors, or any other processor capable of operating as described herein. The central processing unit 221 may utilize instruction level parallelism, thread level parallelism, different levels of cache, and multi-core processors. A multi-core processor may include two or more processing units on a single computing component.

Main memory unit 222 may include one or more memory chips capable of storing data and allowing any storage location to be directly accessed by the microprocessor 221. Main memory unit 222 may be volatile and faster than storage 228 memory. Main memory units 222 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 222 or the storage 228 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 222 may be based on any of the above described memory chips, or any other available memory chips capable of operating as described herein. In the embodiment shown in FIG. 2C, the processor 221 communicates with main memory 222 via a system bus 250 (described in more detail below). FIG. 2D depicts an embodiment of a computing device 200 in which the processor communicates directly with main memory 222 via a memory port 203. For example, in FIG. 2D the main memory 222 may be DRDRAM.

FIG. 2D depicts an embodiment in which the main processor 221 communicates directly with cache memory 240 via a secondary bus, sometimes referred to as a backside bus. In other embodiments, the main processor 221 communicates with cache memory 240 using the system bus 250. Cache memory 240 typically has a faster response time than main memory 222 and is typically provided by SRAM, BSRAM, or EDRAM. In the embodiment shown in FIG. 2D, the processor 221 communicates with various I/O devices 230 via a local system bus 250. Various buses may be used to connect the central processing unit 221 to any of the I/O devices 230, including a PCI bus, a PCI-X bus, or a PCI-Express bus, or a NuBus. For embodiments in which the I/O device is a video display 224, the processor 221 may use an Advanced Graphics Port (AGP) to communicate with the display 224 or the I/O controller 223 for the display 224. FIG. 2D depicts an embodiment of a computer 200 in which the main processor 221 communicates directly with I/O device 230*b* or other processors via HYPERTRANSPORT, RAPIDIO, or INFINIBAND communications technology. FIG. 2D also depicts an embodiment in which local busses and direct communication are mixed: the processor 221 communicates with I/O device 930*a* using a local interconnect bus while communicating with I/O device 230*b* directly.

A wide variety of I/O devices 230*a*-230*n* may be present in the computing device 200. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 230*a*-230*n* may include a combination of multiple input or output devices, including. Some devices 230*a*-230*n* allow gesture recognition inputs through combining some of the inputs and outputs. Some devices 230*a*-230*n* provides for facial recognition which may be utilized as an input for different purposes including authentication and other commands. Some devices 230*a*-230*n* provides for voice recognition and inputs. Additional devices 230*a*-230*n* have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, such as on a table-top or on a wall, and may also interact with other electronic devices. Some I/O devices 230*a*-230*n*, display devices 224*a*-224*n* or group of devices may be augment reality devices. The I/O devices may be controlled by an I/O controller 223 as shown in FIG. 2C. The I/O controller may control one or more I/O devices, such as, e.g., a keyboard 226 and a pointing device 227, e.g., a mouse or optical pen. Furthermore, an I/O device may also provide storage and/or an installation medium 216 for the computing device 200. In still other embodiments, the computing device 200 may provide USB connections (not shown) to receive handheld USB storage devices. In further embodiments, an I/O device 230 may be a bridge between the system bus 250 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 224*a*-224*n* may be connected to I/O controller 223. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 224*a*-224*n* may also be a head-mounted display (HMD). In some embodiments, display devices 224*a*-224*n* or the corresponding I/O controllers 223 may be controlled through or have hardware support for OPENGL or DIRECTX API or other graphics libraries.

In some embodiments, the computing device 200 may include or connect to multiple display devices 224*a*-224*n*, which each may be of the same or different type and/or form. As such, any of the I/O devices 230*a*-230*n* and/or the I/O controller 223 may include any type and/or form of suitable hardware, software, or combination of hardware and software to support, enable or provide for the connection and use of multiple display devices 224*a*-224*n* by the computing device 200. For example, the computing device 200 may include any type and/or form of video adapter, video card, driver, and/or library to interface, communicate, connect or otherwise use the display devices 224*a*-224*n*. In one embodiment, a video adapter may include multiple connectors to interface to multiple display devices 224*a*-224*n*. In other embodiments, the computing device 200 may include multiple video adapters, with each video adapter connected to one or more of the display devices 224a-224n. In some embodiments, any portion of the operating system of the computing device 200 may be configured for using multiple displays 224a-224n. In other embodiments, one or more of the display devices 224a-224n may be provided by one or more other computing devices connected to the computing device 200, via the network 204. In some embodiments software may be designed and constructed to use another computer's display device as a second display device 224a for the computing device 200.

Referring again to FIG. 2C, the computing device 200 may comprise a storage device 228 (e.g. one or more hard disk drives or redundant arrays of independent disks) for storing an operating system or other related software, and for storing application software programs such as any program related to the software 220. Examples of storage device 228 include, e.g., hard disk drive (HDD); optical drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 228 may be non-volatile, mutable, or read-only. Some storage device 228 may be internal and connect to the computing device 200 via a bus 250. Some storage device 228 may be external and connect to the computing device 200 via an I/O device 230 that provides an external bus. Some storage device 228 may connect to the computing device 200 via the network interface 218 over a network 204. Some client devices 200 may not require a non-volatile storage device 228 and may be thin clients or zero clients 202. Some storage device 228 may also be used as an installation device 216, and may be suitable for installing software and programs.

Client device 200 may also install software or application from an application distribution platform. An application distribution platform may facilitate installation of software on a client device 202. An application distribution platform may include a repository of applications on a server 206 or a cloud 208, which the clients 202a-202n may access over a network 204. An application distribution platform may include application developed and provided by various developers. A user of a client device 202 may select, purchase and/or download an application via the application distribution platform.

Furthermore, the computing device 200 may include a network interface 218 to interface to the network 204 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 200 communicates with other computing devices via any type and/or form of gateway or tunneling protocol e.g. Secure Socket Layer (SSL) or Transport Layer Security (TLS). The network interface 218 may comprise a built-in network adapter, network interface card, PCMCIA network card, EXPRESSCARD network card, card bus network adapter, wireless network adapter, USB network adapter, modem or any other device suitable for interfacing the computing device 200 to any type of network capable of communication and performing the operations described herein.

A computing device 200 of the sort depicted in FIGS. 2B and 2C may operate under the control of an operating system, which controls scheduling of tasks and access to system resources. The computing device 200 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 200 can be any workstation, telephone, desktop computer, laptop or notebook computer, netbook, tablet, server, handheld computer, mobile telephone, smartphone or other portable telecommunications device, media playing device, a gaming system, mobile computing device, or any other type and/or form of computing, telecommunications or media device that is capable of communication. The computer system 200 has sufficient processor power and memory capacity to perform the operations described herein. In some embodiments, the computing device 900 may have different processors, operating systems, and input devices consistent with the device.

In some embodiments, the computing device 200 is a gaming system. In some embodiments, the computing device 200 is a digital audio player. Some digital audio players may have other functionality, including, e.g., a gaming system or any functionality made available by an application from a digital application distribution platform. In some embodiments, the computing device 200 is a portable media player or digital audio player supporting file formats including. In some embodiments, the computing device 200 is a tablet. In other embodiments, the computing device 200 is an eBook reader. In some embodiments, the communications device 202 includes a combination of devices, e.g. a smartphone combined with a digital audio player or portable media player. For example, one of these embodiments is a smartphone. In yet another embodiment, the communications device 202 is a laptop or desktop computer equipped with a web browser and a microphone and speaker system, e.g. a telephony headset. In these embodiments, the communications devices 202 are web-enabled and can receive and initiate phone calls. In some embodiments, a laptop or desktop computer is also equipped with a webcam or other video capture device that enables video chat and video call. In some embodiments, the communication device 202 is a wearable mobile computing device.

In some embodiments, the status of one or more machines 202, 206 in the network 204 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Brachytherapy Optimization

Figure 3A:
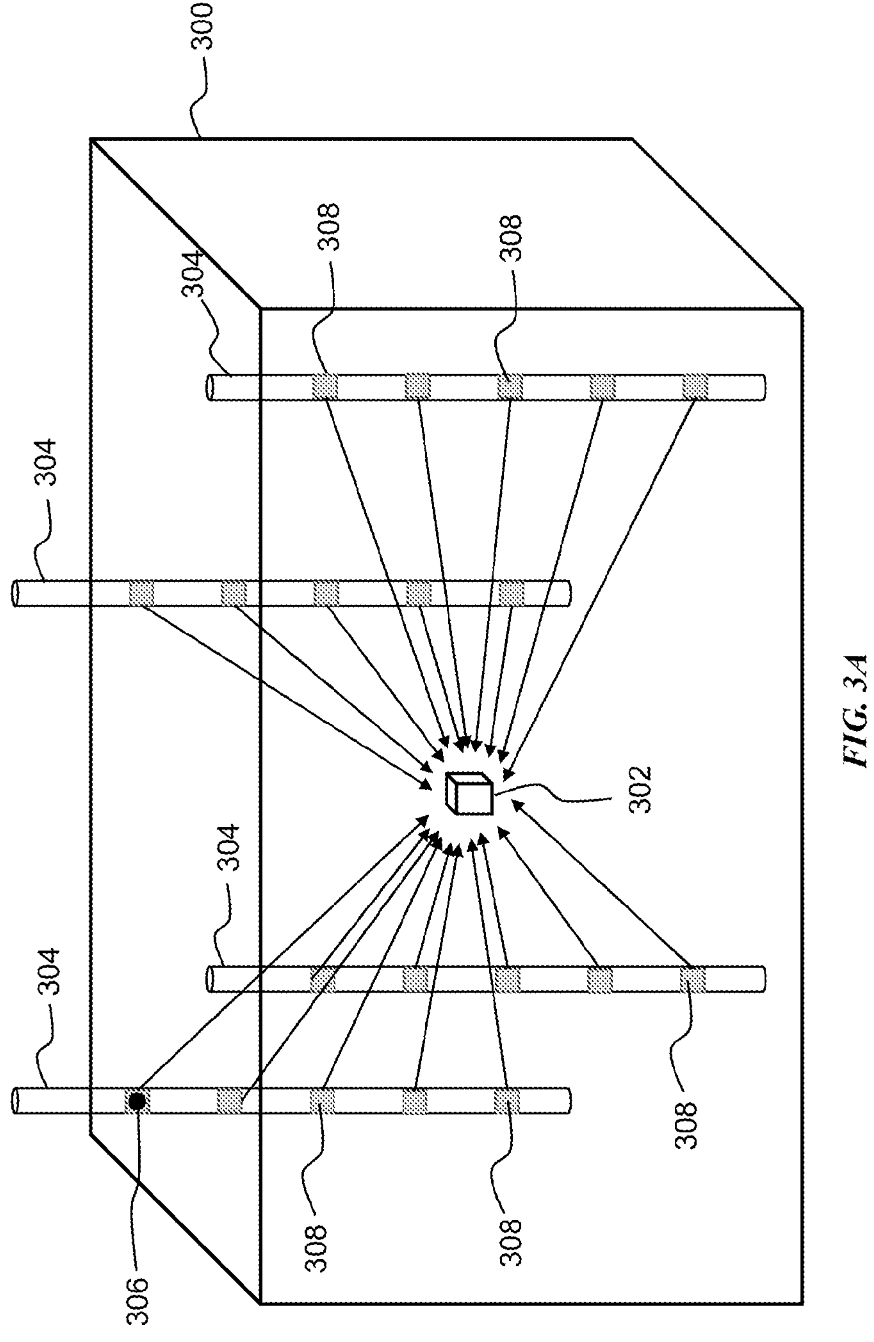
FIGS. 3A and 3B show diagrams illustrating how the radiation dose is distributed within a radiated medium from a mobile radiating seed, according to an example embodiment.
Figure 3B:
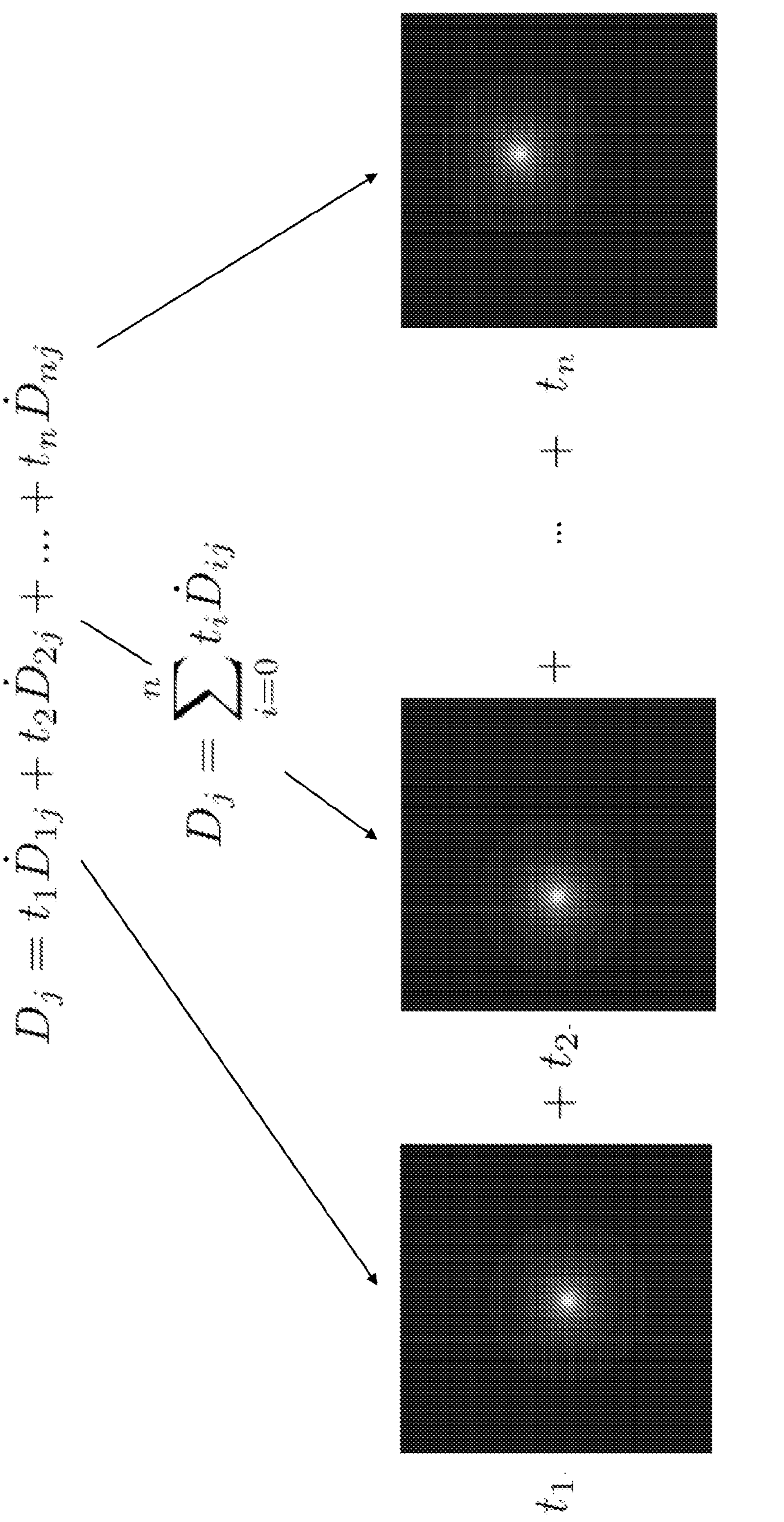

FIGS. 3A and 3B show diagrams depicting how radiation dose is distributed within a radiated medium from a radiating seed, according to an example embodiment. Referring to FIG. 3A, an anatomical region 300 can be discretized in a plurality of voxels 302. A plurality of hollow needles 304 can be inserted into the anatomical region 300. In particular, the needles 304 can be inserted in a target region, e.g., prostate, of the anatomical region 300. The needles 304 can be connected to an afterloader (a device that houses a radioactive seed 306). The needles 304 can be connected to each other via a wire or tube. A drive system can cause the radiation seed 306 to move between dwell positions 308 of the needles 304. Each needle 304 can include a corresponding plurality of dwell positions.

In HDR brachytherapy, the drive system causes the radiation seed to move from one dwell position 308 to another. The drive system causes the radiation seed 306 to dwell at each dwell position 308 for a corresponding time duration (or time intervals) t. The radiation seed 306 has a radiation rate per unit of time. The radiation rate can be defined according to TG-43 as:

$$\dot{D}(r,\theta) = S_K \cdot \Lambda \cdot \frac{G_X(r,\theta)}{G_X(r_0,\theta_0)} \cdot g_X(r) \cdot \phi_{an}(r,\theta),$$

where r is the distance from the radiation seed and $r_0$ is equal to 1 centimeter. The parameter $S_K$ represents a source strength of the radiation seed 306, and $\Lambda$ is a dose rate constant. The function $G_X(r,\theta)$ represents the geometrical fall off of the photon fluence, the function $g_X(r)$ is the radio dose function, and $\phi_{an}(r)$ is the anisotropy factor.

Referring now to FIG. 3B, the total radiation dose to each voxel 302 in the anatomical region 300 is a summation of the dose delivered to the voxel by the radiation seed 306 from each dwell position 308. Specifically, the total radiation dose $D_j$ at some voxel j can be described as:

$$D_j = \sum_{i=1}^{n} t_i \dot{D}_{ij},$$

where i is the dwell position index, n is the total number of dwell positions, $\dot{D}_{ij}$ is the radiation rate for the dwell position i at the voxel j and $t_i$ is the time duration during which the radiation seed 306 dwells at the dwell position i.

In HDR brachytherapy optimization, the task is to determine the time durations $t_i$ which will result in a radiation dose distribution that satisfies the clinical goals and/or the dosimetry constraints. By altering the dwell times $t_i$, one can alter the final dose distribution. Typically, one or more processors, such as processor 220 and/or processing unit 221, can iteratively adjust the dwell times $t_i$ by optimizing an objective function until a final set of dwell times $t_i$ is found that leads to a desired radiation dose distribution or a radiation dose distribution that satisfies a target dose to the target region, such as the prostate, and threshold doses of OARs, such as the urethra and rectum. The set of dwell times $t_i$ is found by minimizing (or maximizing) the objective function.

Figure 4:
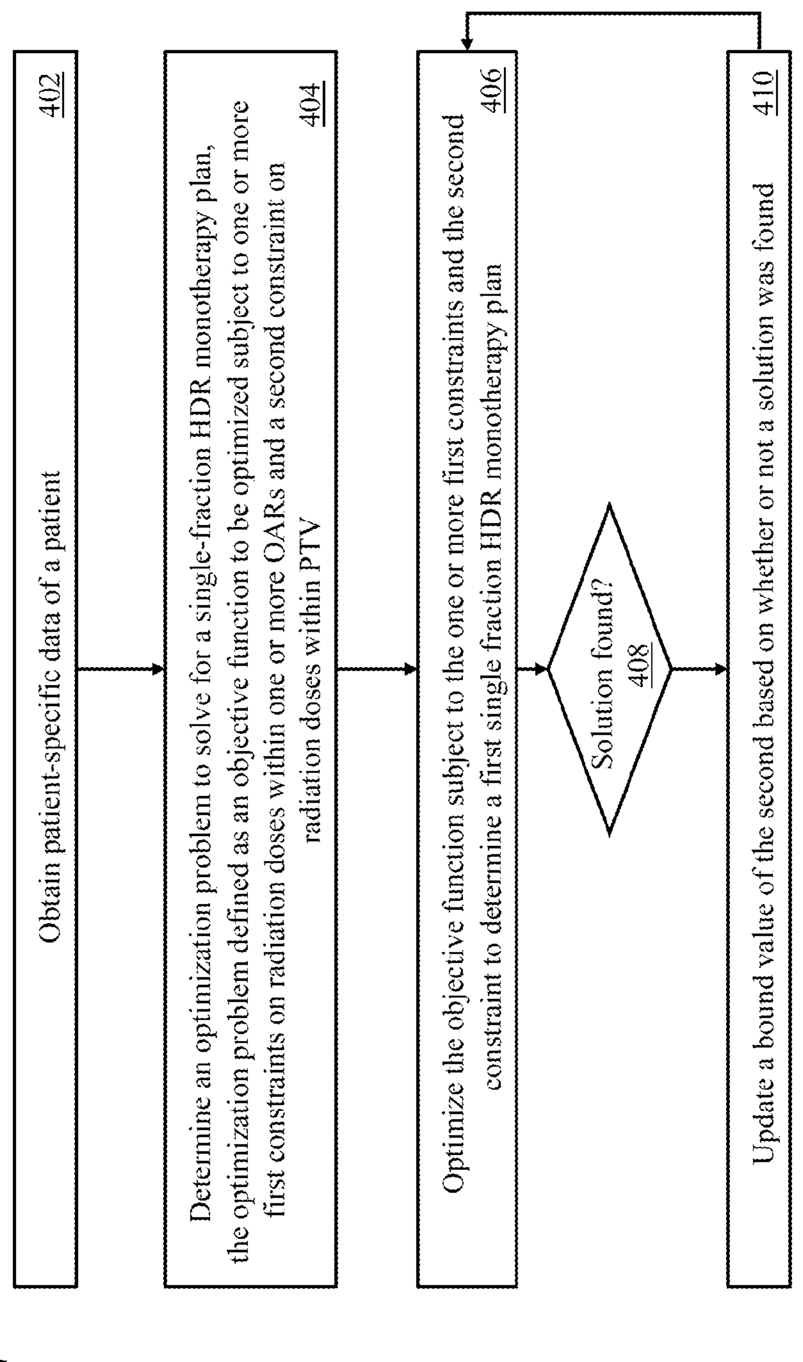
FIG. 4 shows a flow diagram illustrating a method for HDR brachytherapy planning, according to an example embodiment.

FIG. 4 is a flow diagram illustrating a method 400 for HDR brachytherapy planning, according to an example embodiment. The method 400 can be executed on a processing system, such as the processing system described with respect to FIGS. 2A-2D. In particular, the method can be executed by the one or more processors 220 and/or 221. The one or more processors 220 and/or 221 can be configured to execute computer-executable instructions, which are stored on memory, to cause the one or more processors 220 and/or 221 to perform each of the functions of the method 400. In some embodiments, the instructions can be stored as routines, scripts, modules, or code, for execution by the one or more processors 220 and/or 221.

In brief overview, the method 400 can include obtaining patient-specific data of a patient (STEP 402), determining an optimization problem to solve for a single-fraction HDR monotherapy plan where the optimization problem includes an objective function to be optimized subject to one or more first constraints on radiation doses in one or more OARs and a second constraint on radiation doses in a planning target volume (PTV) or target region (STEP 404), and optimizing the objective function subject to first constraint(s) and the second constraint (STEP 406). The method 400 can include determining whether a solution or plan satisfying the first and second constraints is found (STEP 408), and adjusting the second constraint based on whether a solution is found (STEP 410).

The method 400 can include one or more processors 220 and/or 221 obtaining patient-specific data of a patient (STEP 402). The one or more processors 220 and/or 221 can receive, as input, imaging data and radiation dose data or clinical goals. The one or more processors 220 and/or 221 can be configured to execute computer-executable instructions to receive, as input, imaging data and radiation dose data or clinical goals. The imaging data can include X-ray images, ultrasound images, magnetic resonance (MR) images, optical tomography images, other type of medical images or a combination thereof. In some implementations, the input medical images can include contours of different regions or organs added by a physician, such as PTV (e.g., prostate) and OARs such as rectum, bladder and/or urethra. The one or more processors 220 and/or 221 can generate, using the input imaging data, a three-dimensional (3D) structure of the anatomical region including the PTV, the OARs and normal tissue in between or around the PTV and OARs. In some implementations, the one or more processors 220 and/or 221 can receive the 3D structure as input. The 3D structure can include a PTV structure and OAR structures. The 3D structure can include a plurality of voxels. The resolution of the 3D structure can be defined by or equal to the resolution of the input medical images.

The patient-specific input data can include data indicative of the positions of the needles 304 within the 3D structure 300 and dwell positions within the needles 304. Each needle 304 can include an X number of dwell positions or locations where the radioactive seed will "dwell" and deliver radiation dose. In some implementations, the one or more processors 220 and/or 221 can determine and/or optimize the positions of the needles 304 and/or the dwell positions 308.

The one or more processors 220 and/or 221 can define or generate the voxels of the 3D structure 300. In some embodiments, the one or more processors 220 and/or 221 can be configured to execute computer-executable instructions to define or generate the voxels of the 3D structure 300. In some implementations, the one or more processors 220 and/or 221 can resample or downsample the 3D structure 300. In some embodiments, the one or more processors 220 and/or 221 can be configured to execute computer-executable instructions to resample or downsample the 3D structure 300. For example, the initial resolution of the 3D structure 300 or the resolution of the input medical images can be a fine resolution in the range of a fraction of a millimeter. Such fine resolution may not add any value with respect to the treatment planning. The one or more processors 220 and/or 221 can define the voxels or downsample the voxels 302 of the 3D structure 300 to achieve a resolution of 1 mm, for example. For example, each voxel 302 can be 1 mm×1 mm×1 mm. The dowsampling of the voxels 302 or the 3D structure 300 reduces the complexity of the treatment planning optimization significantly.

In some implementations, the one or more processors 220 and/or 221 can adjust or alter one or more structures, e.g., PTV and/or OAR structure(s), within the 3D structure 300. In some embodiments, the one or more processors 220 and/or 221 can be configured to execute computer-executable instructions to adjust or alter one or more structures, e.g., PTV and/or OAR structure(s), within the 3D structure 300. For example, the one or more processors 220 and/or 221 can apply one or more morphological operations, such as dilation, erosion and/or Boolean operations, on the one or more structures, e.g., PTV and/or OAR structure(s). In some implementations, the one or more processors 220 and/or 221 can expand the urethral structure, e.g., by 1 mm. Since the urethra passes through the prostate, expanding the urethral structure facilitates satisfying dosimetry constraints of the urethra. Also, the expansion of any structure allows for curing or handling any uncertainty or errors in the contour of the structure. The one or more processors 220 and/or 221 can apply an expansion or dilation to the rectum. In some implementations, the one or more processors 220 and/or 221 can determine a shell of or around the PTV (e.g., prostate). For instance, the one or more processors 220 and/or 221 can expand or dilate the PTV, e.g., by one or more voxels, and subtract the dilated PTV from the original PTV to determine a shell structure around the PTV. The one or more processors 220 and/or 221 can define one or more dosimetry constraints within the shell structure around the PTV.

Volume or structure expansion helps push for or enforce conformity. In other words, the expanded region can provide flexibility and facilitate satisfying radiation dose constraints associated with the corresponding structure. In some implementations, no radiation dose (or radiation dose constraint) may be specified or enforced for the expanded voxels. For example, for the PTV, a corresponding expanded region can allow for radiation dose spill within the expanded region of the PTV. In some implementations, the structure expansion or dilation can be anisotropic. Anisotropic expansion can allow radiation dose to spill more anteriorly and laterally for example than posteriorly and superiorly The one or more processors 220 and/or 221 can determine, for each structure, the corresponding set of voxels defining the structure. In some embodiments, the one or more processors 220 and/or 221 can be configured to execute computer-executable instructions to determine, for each structure, the corresponding set of voxels defining the structure. For example, the one or more processors 220 and/or 221 can determine for the PTV and each OAR the corresponding set of voxels. For any structure, the corresponding set of voxels can be defined as all the voxels in the structure. A radiation constraint within a given structure can be formulated as a constraint for each voxel in the structure.

The patient-specific input data can include clinical goals for the PTV, OARs and/or other regions. For example, the clinical goals can include the D90 (e.g., radiation dose for 90%) of the PTV. The clinical goals can include a PTV radiation dose. In some implementations, the PTV can have multiple radiation dose goals or constraints. The clinical goals can include at least one radiation dose goal or constraint for each OAR region or structure. For example, the clinical goal(s) for an OAR structure can include a maximum radiation dose not to be exceeded by any voxel in the OAR structure, a radiation dose to be received by a percentage of the voxels or a combination thereof.

The method 400 can include determining an optimization problem to solve for a single-fraction HDR monotherapy plan where the optimization problem includes an objective function to be optimized subject to one or more first constraints on radiation doses in one or more OARs and a second constraint on radiation doses in a planning target volume (PTV) or target region (STEP 404). In some embodiments, the one or more processors 220 and/or 221 can be configured to determine the optimization problem to solve for a single-fraction HDR monotherapy plan. The objective function can be defined as the radiation dose within the PTV that is to be maximized. In some implementations, the objective function can be defined as the radiation dose discrepancy with regard to the prescription dose or target dose within the PTV. For example, the objective function can be defined as the sum of differences between the target dose and dose at each voxel that is falling short of the target dose. The target dose can be equal to the prescription dose or can be defined as a percentage (e.g., 100% or 120%) of the prescription dose.

For example, if we say "$D_j$" be the radiation of given voxel "j" in the PTV, e.g., prostate. The one or more processors 220 and/or 221 can define for each voxel j define $Z_j$ as $Z_j$=PTV target dose−$D_j$, for voxels where $D_j$<PTV target dose. Otherwise, $Z_j$ be equal to zero. The one or more processors 220 and/or 221 can define the objective function as:

$$C = \frac{1}{M}\sum_{j=1}^{L} Z_j,$$

where L is the total number of voxels in the PTV. The parameter M can be an integer representing the number of voxels in the PTV with a corresponding radiation dose below the target dose for the PTV.

The prescription dose (or target dose) for the PTV can be specified as part of the input data, e.g., by a physician. The goal is to push all voxels in the PTV to have a radiation dose that is equal to or greater than the target dose. If the voxel is above the target dose, no penalty is applied to the corresponding radiation dose. In brachytherapy, due to inverse square law, voxels in the proximity of the dwells will be much hotter (very high radiation dose) than those farther away. It's typically difficult to limit hot voxels in the PTV, as that is how radiation is delivered. As such, hot voxels in the PTV are not penalized since those voxels will eventually exist and in the case of dose escalation are also not discouraged.

The radiation dose constraints can include maximum dose constraints, volumetric constraints or a combination thereof. For example, an OAR structure, e.g., urethra or rectum, can have a maximum radiation dose constraint specifying that the maximum radiation dose may not be exceeded by any voxel in the OAR structure. The OAR structure may have a volumetric dose constraint specifying a radiation dose to be received by a subset or percentage of voxels in the OAR structure, e.g., D90, D50, etc.

In some implementations, the one or more processors 220 and/or 221 can define or determine a shell region (or shell structure or rind) around the PTV. The shell region may be or may not be immediately around the PTV. For example, there may be some tissue region between the PTV and the shell region. The shell region can include one or more OAR regions. The one or more processors 220 and/or 221 can determine a third radiation constraint within the shell region. For example, the third constraint can be defined to prevent dose spill within the shell region. In other words, radiation doses with the shell region can be forced to be below the target dose of the PTV. The one or more processors can optimize the objective function subject to the first constraints of the OARs, the second constraint(s) of the PTV and the third constraint of the shell region.

In some implementations, the one or more processors 220 and/or 221 can define or determine one or more additional constraints on dwell time durations. For example, one constraint can specify that dwell time durations for consecutive (or neighboring) dwell positions within a needle may not differ by more than a predefined threshold value. Assuming that there are 10 dwell position per needle, a dwell time duration defined as 0, 0, 0, 0, 0, 10, 0, 0, 0, 0 can become 0, 0, 0, 0, 1, 8, 1, 0, 0, 0 if the constraint specifies that the difference in dwell time duration for neighboring dwells has to be less than 10 s. If the constraint indicates that the difference in dwell time duration for neighboring dwells has to be less than 5 s, the dwell time duration 0, 0, 0, 0, 0, 10, 0, 0, 0, 0 can become 0, 0, 0, 0, 2, 8, 2, 0, 0, 0. The constraint(s) on the dwell time durations can be built into the optimization rather than applied after as some kind of smoothing factor. That is, the one or more processors 220 and/or 221 can optimize the objective function with the constraint(s) on the dwell time durations as additional constraint(s) to be satisfied as part of the optimization. Such constraints make the final treatment plans more robust as small variation/uncertainty in the dwell positions won't lead to large actual dosimetric differences.

The method 400 can include the one or more processors 220 and/or 221 optimizing the objective function subject to first constraint(s) and the second constraint (STEP 406). Optimizing the objective function can include, for example, minimizing the objective function C defined above subject to the constraints of the OARs and the constraint(s) of the PTV. The one or more processors 220 and/or 221 can use linear programming to optimize the objective function. In one or more processors 220 and/or 221 can optimize the objective function within or using the downsampled 3D structure of the anatomical region (e.g., the 3D structure with coarse or lower resolution). The one or more processors 220 and/or 221 can use linear programming to solve the optimization problem. Solving the optimization problem involves solving for the dwell time durations.

Furthermore, the one or more processors 220 and/or 221 can speed the optimization by reducing the number of constraints. For example, instead of defining a radiation constraint for each voxel in the PTV, the one or more processors 220 and/or 221 can define the constraint for a sampled set (e.g., a percentage) of the voxels within the PTV. In brachytherapy, the radiation is delivered from each seed and is distributed according to an inverse square of the distance from the seed. Therefore, the radiation dose is expected to be approximately the same at neighboring voxels. The one or more processors 220 and/or 221 can reduce complexity significantly by considering a sampled set of the voxels instead of all the voxels. In other words, optimizing the radiation dose for one voxel is approximately equivalent to optimizing for two multiple neighboring voxels. The sampling rate can be selected or provided as input by a user.

The method 400 can include the one or more processors 220 and/or 221 determining whether a solution or plan satisfying the first and second constraints is found (STEP 408), adjusting the second constraint based on whether a solution is found (STEP 410). The one or more processors 220 and/or 221 can run or execute the optimization (e.g., using linear programming) of the objective function subject to the first second and any other defined constraints. The optimization can include one or more stopping criteria. Once the optimization is complete, the one or more processors 220 and/or 221 whether the treatment plan achieved through the optimization satisfies the first and second constraints (and possibly any other constraints). The one or more processors 220 and/or 221 can update or adjust the second constraint associated with the PTV depending on whether the first and second constraints (and possibly any other constraints) are satisfied.

Figure 5:
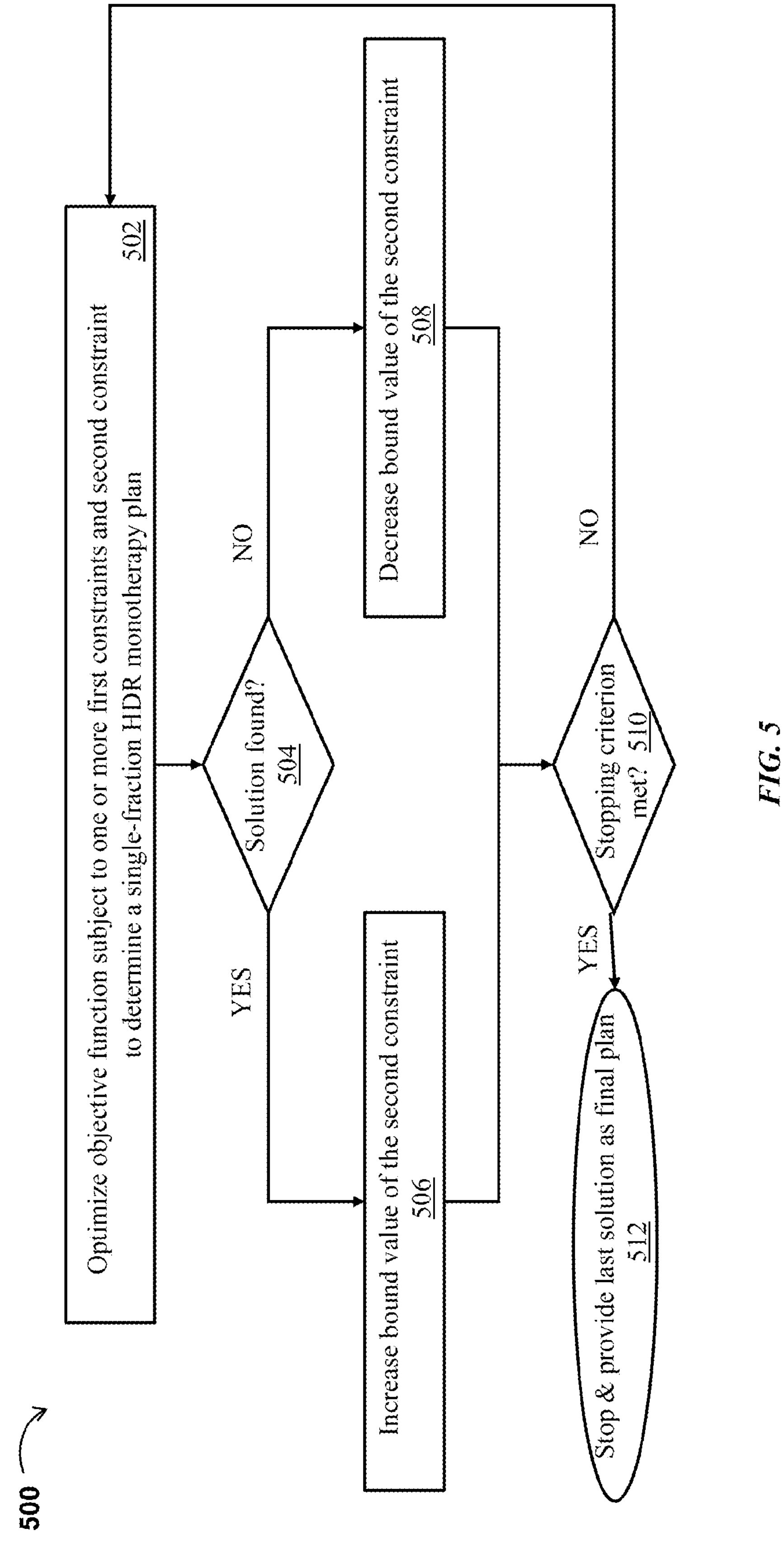
FIG. 5 shows a flow diagram illustrating another method for HDR brachytherapy planning, according to an example embodiment.

The one or more processors 220 and/or 221 can adjust the second constraint in one way if the treatment plan satisfies the first and second constraints, and adjust the second constraint in a different way if the treatment plan achieved through the optimization does not satisfy the first and second constraints. Adjusting the second constraint can include adjusting a radiation dose bound value of the second constraint. The idea is to strictly enforce the constraints (e.g., as hard constraints) of the OARs and incrementally escalate the radiation dose for the PTV in order to achieve the highest possible radiation dose distribution within the PTV while strictly satisfying the constraints in the OARs (and possibly in other regions). The second constraint for the PTV can be viewed as an iterative constraint that can be adjusted after each optimization. FIG. 5 shows an example implementation of the incremental or iterative escalation of radiation doses in the PTV.

FIG. 5 shows a flow diagram illustrating another method 500 for HDR brachytherapy planning, according to an example embodiment. The method 500 can be viewed as an implementation of the steps 406-410 of FIG. 4. In brief overview, the method 500 can include optimizing the objective function subject to first constraint(s) and the second constraint (STEP 502), and determining whether a solution or plan satisfying the first and second constraints is found (STEP 504). The method 500 can include increasing the bound value of the second constraint upon determining that a solution is found (STEP 506), and decreasing the bound value of the second constraint upon determining that no solution is found (STEP 508). The method 500 can determining whether a stopping criterion is met (STEP 510), and iterating back to step 502 if the stopping criterion is not met.

If the stopping criterion is met, the method 500 ends and the final treatment plan is provided as output (STEP 512).

The method 500 can include the or more processors 220 and/or 221 optimizing the objective function subject to first constraint(s) and the second constraint (STEP 502), and determining whether a solution or plan satisfying the first and second constraints is found (STEP 504). The steps 502 and 504 of method 500 are similar to steps 406 and 408 of method 400 in FIG. 4.

The method 500 can include the or more processors 220 and/or 221 increasing the bound value of the second constraint upon determining that a solution is found (STEP 506), and decreasing the bound value of the second constraint upon determining that no solution is found (STEP 508). The bound value can be a target radiation dose of the PTV or a radiation dose defined in terms of the target radiation dose. When a treatment plan that satisfies the first and second constraints is found, that indicate that there may be room to escalate or increase the target dose or a lower bound dose of the PTV. In other words, the optimization can be re-run or re-executed with a higher target dose or with a higher lower bound of a PTV constraint (e.g., a volumetric constraint). Therefore, the one or more processors 220 and/or 221 can increase the bound value of the second constraint.

In the case where no plan satisfying the first and second constraints is found, the one or more processors 220 and/or 221 can infer that the used radiation dose bound of the second constraint is too high and should be reduced. Therefore, the one or more processors 220 and/or 221 can decrease the bound value (e.g., a lower bound value of the second constraint).

The method 500 can include the one or more processors 220 and/or 221 determining whether a stopping criterion is met (STEP 510), and iterating back to step 502 if the stopping criterion is not met. If the stopping criterion is met, the method 500 ends and the last treatment plan that satisfies the first and second constraints can be provided as output (STEP 512). The stopping criterion can be defined in terms of the difference between consecutive bound values of the second constraint. For example, if the difference between consecutive bound values is less than some threshold value $\delta$, the one or more processors 220 and/or 221 stop iterating (STEP 512) and provide the last found plan that satisfies the first and second constraints (and possibly other constraints) as output.

In some implementations, the one or more processors 220 and/or 221 can update the bound value by defining a range for the bound value, e.g., $[X_{min}, X_{max}]$. At the initial iteration, the one or more processors 220 and/or 221 can select the bound value as the midpoint of $[X_{min}, X_{max}]$, which is $(X_{min}+X_{max})/2$. For example, considering D90 for the PTV, the one or more processors 220 and/or 221 can define $X_{min}$ to be equal to 0 and define $X_{max}$ to be equal to 500% prescription dose. At any following iteration, if no solution is found, the one or more processors 220 and/or 221 can replace $X_{max}$ with the midpoint $(X_{min}+X_{max})/2$. If a solution is found, the one or more processors 220 and/or 221 can replace $X_{min}$ with the midpoint $(X_{min}+X_{max})/2$. The one or more processors 220 and/or 221 can define the new bound value as the midpoint of the new interval. The one or more processors 220 and/or 221 can keep iterating until the difference between successive midpoints is smaller than size of the interval becomes smaller than the threshold value $\delta$ or until the size of the interval becomes smaller than some other threshold.

The methods 400 and 500 move away from having adjustable weights and instead strictly enforce constraints (bounded) and push to find the maximal dose to the PTV, e.g., prostate. Complementary tools can assist the optimizer to generate useful contours structures automatically as well as suggest needle placements.

Given the linear optimization approach described above, one technical problem of implementing volumetric constraints is how to keep the optimization problem linear. The issue here is that a priori one can't know what voxels to target to consider into our linear problem. To do this precisely every single combination of voxels that equaled our volumetric constraint would need to be checked, which is computationally infeasible. In brachytherapy the maximal dose constraint can be correlated with the DXcc (dose delivered to the hottest X cubic centimeters) as the delivery of radiation comes internally from dwells, and the hottest voxels will be surrounded by similarly hot voxels. Therefore, by minimizing a hot voxel, there is a weakly implied constraint on the volume constraints. This alone will greatly reduce volumetric dose, but to enforce these more strongly the one or more processors can implement the following. The one or more processors 220 and/or 221 can random sample subsets of Xcc voxels in each OAR that set to a corresponding dose constraint. Given the dose distribution of brachytherapy, even doing several hundred subsets begins to approximate a volumetric constraint. The one or more processors 220 and/or 221 can find the nearest voxels to dwells, and dilate dwells by several voxels if the expanded region overlaps with a contour of an OAR (e.g., urethra). The one or more processors 220 and/or 221 can dilate until the volume of the overlap equals the volumetric constraint (or the percentage volume of the volumetric constraint). While this approach does not maximally enforce the constraint, it does reduce the solution space. For OARs such as the bladder and rectum, this approach can replicate the true volumetric constraints. Voxels far from the dwells will receive less radiation dose than those nearby. By focusing on the proximal voxels, the one or more processors 220 and/or 221 can ensure selecting the voxels to receive the most dose.

In some implementations, the one or more processors 220 and/or 221 can run the optimization initially with no volumetric constraints, and find the set of OAR voxels that are "hot", e.g., having a relatively high dose and are the only voxels that contribute to the volumetric constraints. The one or more processors 220 and/or 221 can define a set of hottest voxels in an OAR as a set of potentially hot voxels plus minor expansion. Such voxels will be the closes to the dwells. The set of "hot" voxels is much less than the total voxels in the OAR. By forcing each subset to meet the OAR constraint(s) during optimization, then the one or more processors 220 and/or 221 can ensure satisfying the volumetric constraint(s). In the case of a prostate treatment, such approach is most helpful for the urethra.

The treatment plans provided by the methods described herein can be used as single-fraction monotherapy plans. However, the same approach can also be used for other HDR Brachytherapy treatment (e.g., not necessarily single-fraction and/or monotherapy).

C. Experimental Results

Table 1 below shows simulation results for ERBT and brachytherapy plans determined according to methods described herein. The results in Table 1 shows that the brachytherapy plans determined according the methods described herein outperform ERBT, and can be used as single-fraction monotherapy treatment plans.

TABLE 1

| Contour | Metric | External Beam SDRT median (range) | Brachytherapy median ± std dev (range) |
|---|---|---|---|
| PTV (EBRT = Prostate + 2 mm; Brachy = Prostate with no margin) | D50% | 24.9 (24.7-25.1) | 27.2 ± 1.0 (25.5-30.9) |
| | Dmean | 24.5 (24.3-24.7) | 31.4 ± 1.7 (29.1-39.0) |
| | D95% | 22.1 (20.5-22.9) | 22.1 ± 1.0 (18.6-23.6) |
| | D2% | 25.6 (25.4-25.8) | 73.3 ± 11.4 (56.8-118) |
| | V24Gy | 84.8 (76.1-90.1) | 79.8 ± 5.8 (63.3-93.6) |
| | V21.6Gy | 96.2 (92.2-98.4) | 96.2 ± 2.9 (86.4-99.4) |
| Urethra | D1cc | 18.5 (17.3-18.4) | 10.6 ± 3.8 (10.7-19) |
| Rectal Wall | D1cc | 18.8 (18.6-19.1) | 18.2 ± 1.9 (9.7-21.1) |

Figure 6A:
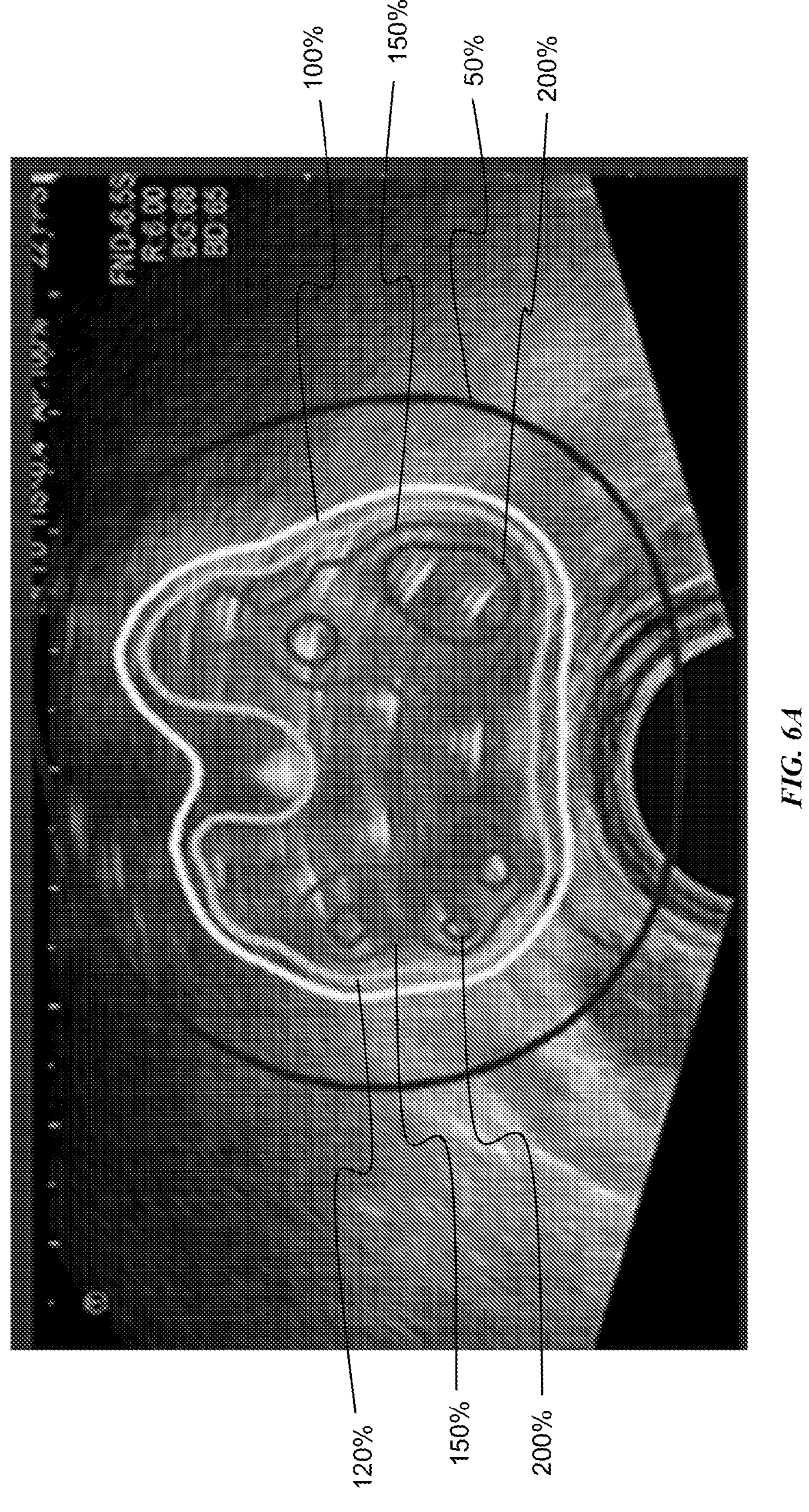
FIGS. 6A-6D show ultrasound images of a prostate with contours depicting simulation results of various single-fraction HDR monotherapy plans generated according to the methods in FIGS. 4 and 5.
Figure 6B:
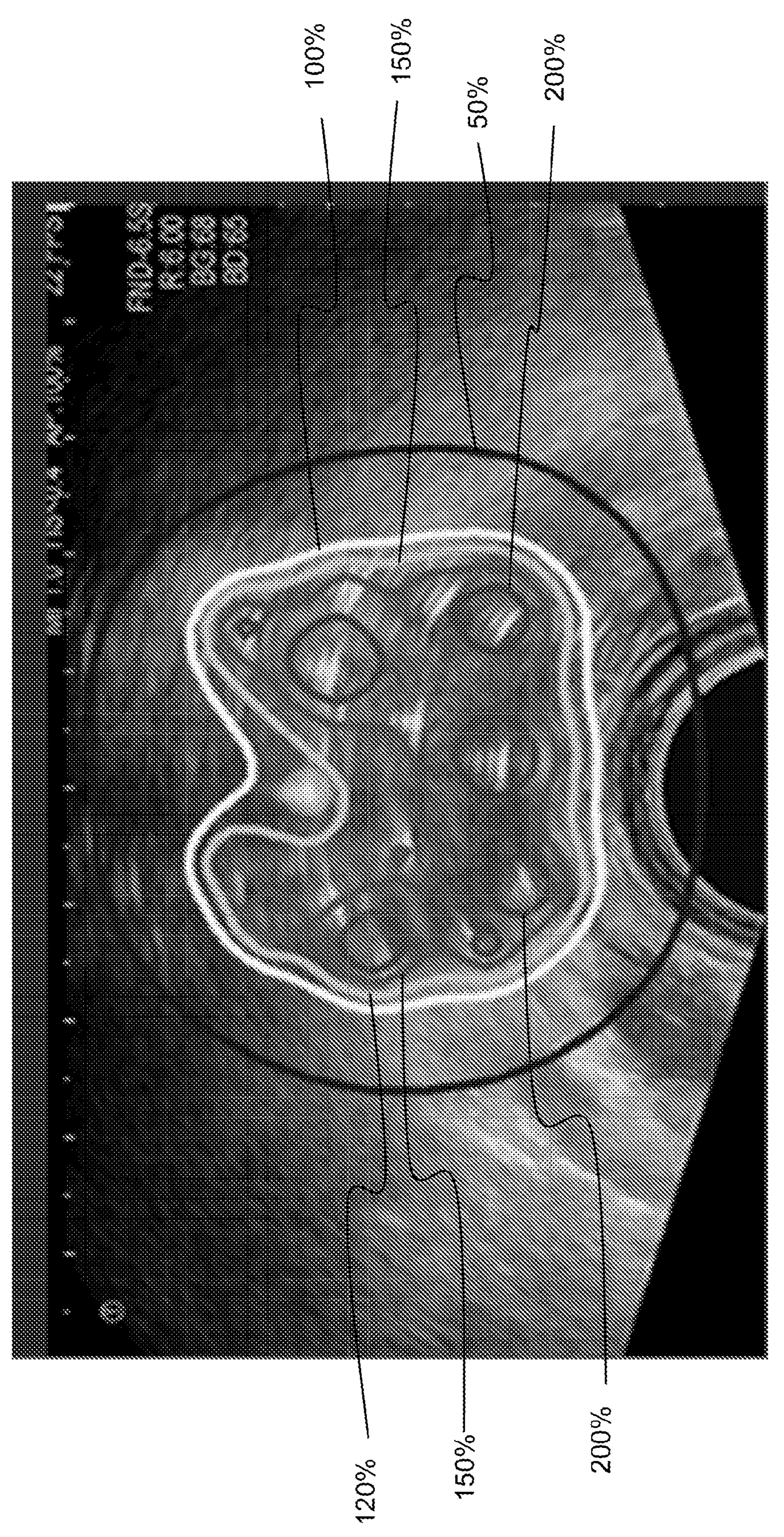
Figure 6C:
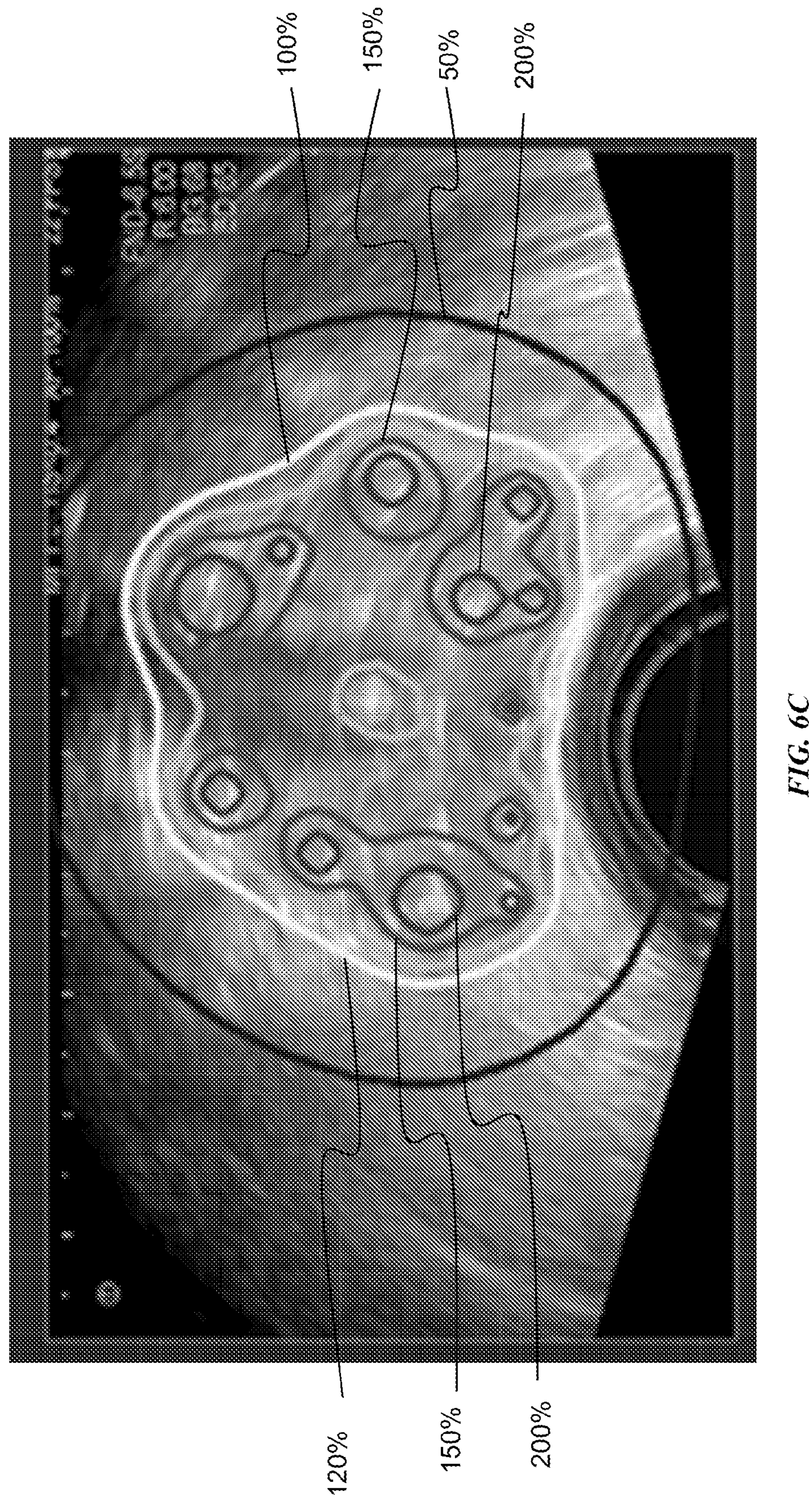
Figure 6D:
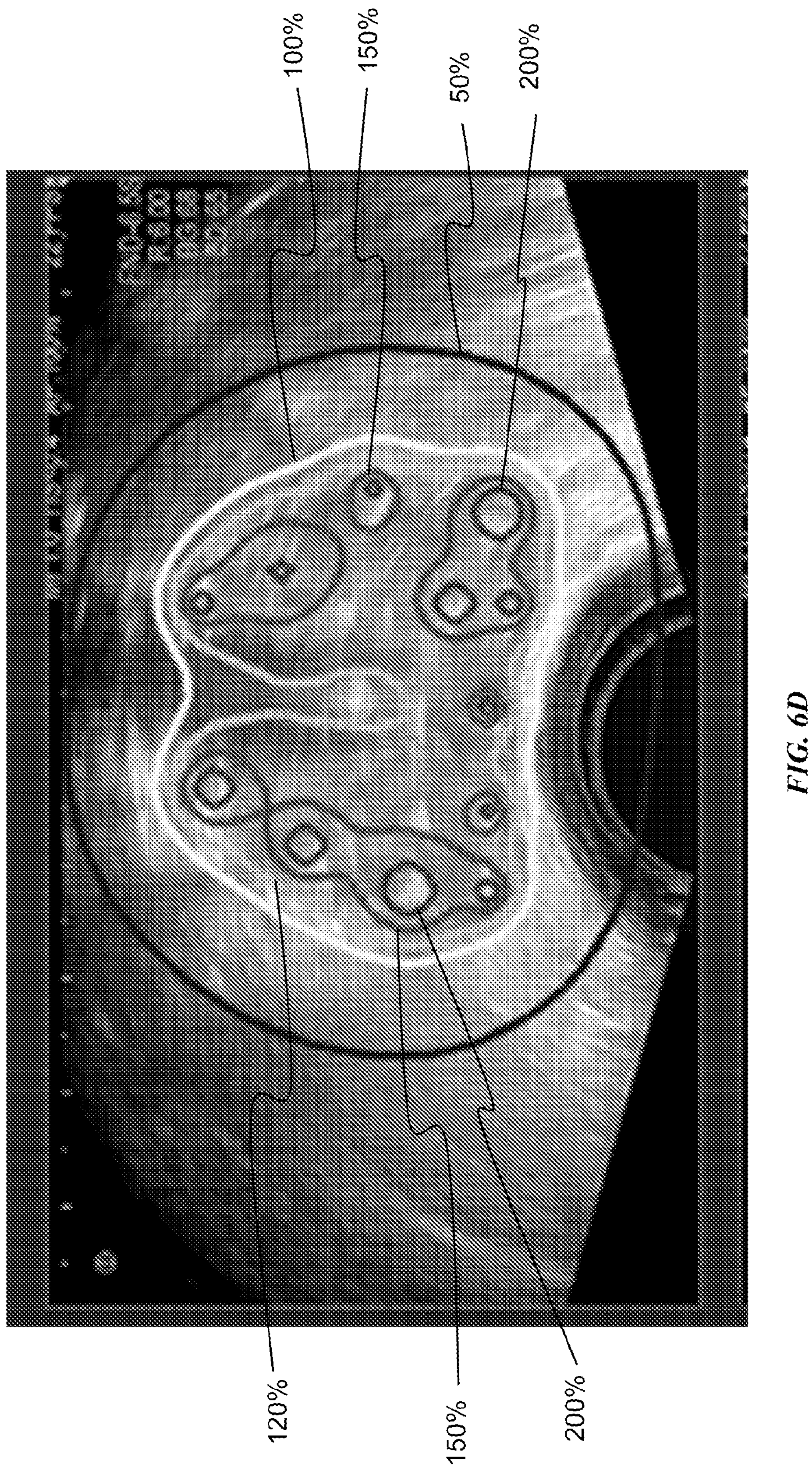

FIGS. 6A-6D show ultrasound images of a prostate with contours depicting simulation results of various single-fraction HDR monotherapy plans generated according to the methods described herein. The 50% contour is indicative of the volume receiving 50% of the prescription dose, the 100% contour is indicative of the volume receiving 100% of the prescription dose, the 120% contour is indicative of the volume receiving 120% of the prescription dose, the 150% contours are indicative of the volumes receiving 150% of the prescription dose, and the 200% contours are indicative of the volumes receiving 200% of the prescription dose. The plans corresponding to FIGS. 6B and 6D include additional constraints on how far can the prescription dose spill out of the prostate. The prostate is shown with a darker gray region, and the 100% contours in FIGS. 6B and 6D are more confined to the prostate regions than the 100% contours in FIGS. 6A and 6C, where there is more radiation dose spill outside the prostate.

Figure 7:
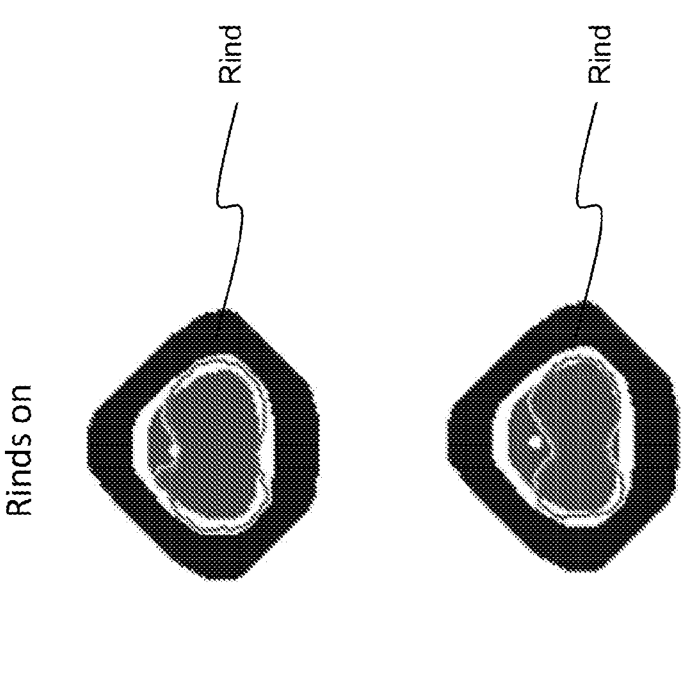
FIG. 7 shows simulation results with and without rind.
Figure 7:
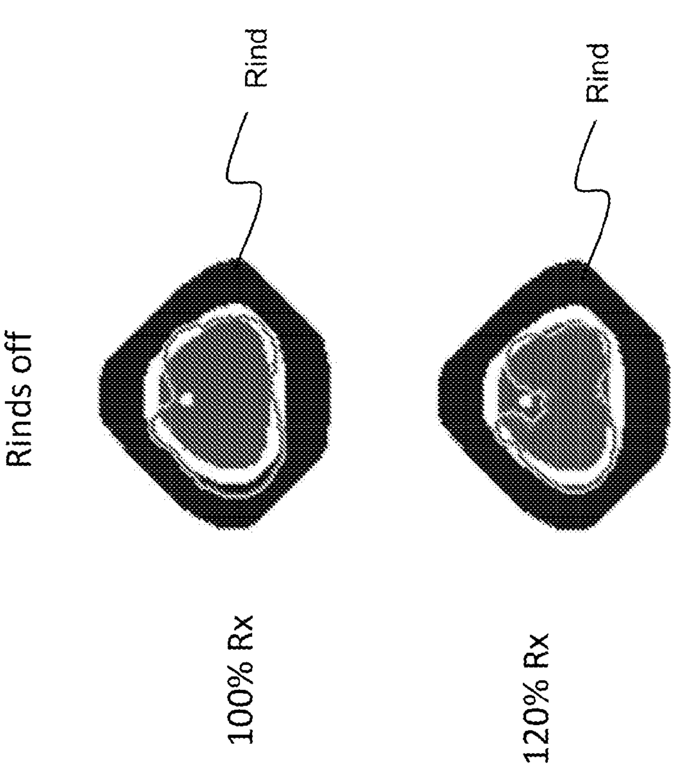

FIG. 7 shows simulation results with and without rind. The rind can be viewed as a shell region defined around the PTV, e.g. prostate, and used to enforce no radiation dose spill within the shell region. Radiation dose spill refers to radiation doses greater than or equal to the prescription dose. The contour shown in the images represents the region receiving the prescription dose or a higher dose. The images on the left side depicts simulation results where the rind constraint is not used. As a results, the contours indicative of the regions receiving the prescription dose overlap with the rind. On the right side, the rind constraint (to prevent radiation dose spill) is enforced, and the contours do not overlap with the rind.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method for high-dose-rate (HDR) brachytherapy planning, the method comprising:

obtaining, by one or more processors, patient specific data of a patient, the patient specific data including information of an anatomical region of the patient having a planning target volume (PTV) and one or more organ-at-risk (OAR) regions, and indications of a plurality of clinical goals;

determining, by the one or more processors using the patient specific data, an optimization problem to solve for a single-fraction HDR monotherapy plan, the optimization problem including an objective function to be optimized subject to one or more first constraints on radiation doses within the one or more OAR regions and a second constraint on radiation doses within the PTV;

optimizing, by the one or more processors, the objective function subject to the one or more first constraints and the second constraint;

determining, by the one or more processors, whether the single-fraction HDR monotherapy plan satisfies the one or more first constraints and the second constraint;

updating, by the one or more processors, a bound value of the second constraint based on whether the single-fraction HDR monotherapy plan satisfies the one or more first constraints and the second constraint; and optimizing, by the one or more processors, the objective function subject to the one or more first constraints and the second constraint with the updated bound value.

2. The method of claim 1, wherein updating the bound value of the second constraint includes:

decreasing the bound value of the second constraint upon determining that the single-fraction HDR monotherapy plan does not satisfy the one or more first constraints or the second constraint; and increasing the bound value of the second constraint upon determining that the single-fraction HDR monotherapy plan satisfies the one or more first constraints or the second constraint.

3. The method of claim 1, comprising iteratively repeating (i) determining whether the single-fraction HDR monotherapy plan satisfies the one or more first constraints and the second constraint, (ii) updating of the bound value of the second constraint and (iii) optimizing the objective function subject to the one or more first constraints and the second constraint with the updated bound value until one or more stopping criteria are met.

4. The method of claim 3, wherein iteratively optimizing the objective function subject to the one or more first constraints and the second constraint with the updated bound value includes:

at each iteration, identifying voxels in the PTV having radiation doses below a predefined radiation dose value;

determining, for each identified voxel in the PTV, a corresponding radiation dose difference between the predefined radiation dose value and a respective radiation dose at the identified voxel; and minimizing a sum of corresponding radiation dose differences of the identified voxels in the PTV subject to the one or more first constraints and the second constraint with the updated bound value.

5. The method of claim 1, wherein optimizing the objective function subject to the one or more first constraints and the second constraint includes using linear programming.

6. The method of claim 1, wherein optimizing the objective function subject to the one or more first constraints and the second constraint includes solving for dwell time durations for a plurality of dwell positions, and wherein the optimization problem further includes a constraint on dwell time durations for neighboring dwell positions.

7. The method of claim 1, wherein the PTV includes a prostate region of the patient.

8. The method of claim 1, comprising:

determining, by the one or more processors, a region around the PTV, wherein the optimization problem further includes a third constraint on radiation doses within the region around the PTV; and optimizing, by the one or more processors, the objective function subject to the one or more first constraints, the second constraint and the third constraint.

9. The method of claim 1, comprising:

identifying, for each OAR region, a sub-region of the OAR region expected to have highest radiation doses in the OAR region; and optimizing the objective function subject to the one or more first constraints applied to radiation doses within the sub-regions of the OAR regions.

10. The method of claim 1, comprising:

generating, by the one or more processors and using the patient specific data, a three-dimensional (3D) structure representing an anatomical region of the patient;

downsampling, by the one or more processors, the 3D structure; and optimizing, by the one or more processors, the objective function within the downsampled 3D structure.

11. A system for high-dose-rate (HDR) brachytherapy planning, comprising:

one or more processors; and a memory storing computer instructions, the computer instructions when executed by the one or more processors cause the one or more processors to:

obtain patient specific data of a patient, the patient specific data including information of an anatomical region of the patient having a planning target volume (PTV) and one or more organ-at-risk (OAR) regions, and indications of a plurality of clinical goals;

determine, using the patient specific data, an optimization problem to solve for a single-fraction HDR monotherapy plan, the optimization problem including an objective function to be optimized subject to one or more first constraints on radiation doses within the one or more OAR regions and a second constraint on radiation doses within the PTV;

optimize the objective function subject to the one or more first constraints and the second constraint;

determine whether the single-fraction HDR monotherapy plan satisfies the one or more first constraints and the second constraint;

update a bound value of the second constraint based on whether the single-fraction HDR monotherapy plan satisfies the one or more first constraints and the second constraint; and optimize the objective function subject to the one or more first constraints and the second constraint with the updated bound value.

12. The system of claim 11, wherein in updating the bound value of the second constraint the one or more processors are configured to:

decrease the bound value of the second constraint upon determining that the single-fraction HDR monotherapy plan does not satisfy the one or more first constraints or the second constraint; and increase the bound value of the second constraint upon determining that the single-fraction HDR monotherapy plan satisfies the one or more first constraints or the second constraint.

13. The system of claim 11, wherein the one or more processors are configured to iteratively (i) determine whether the single-fraction HDR monotherapy plan satisfies the one or more first constraints and the second constraint, (ii) update the bound value of the second constraint and (iii) optimize the objective function subject to the one or more first constraints and the second constraint with the updated bound value until one or more stopping criteria are met.

14. The system of claim 13, wherein to iteratively optimize the objective function subject to the one or more first constraints and the second constraint with the updated bound value the one or more processors are configured to:

at each iteration, identify voxels in the PTV having radiation doses below a predefined radiation dose value;

determine, for each identified voxel in the PTV, a corresponding radiation dose difference between the predefined radiation dose value and a respective radiation dose at the identified voxel; and minimize a sum of corresponding radiation dose differences of the identified voxels in the PTV subject to the one or more first constraints and the second constraint with the updated bound value.

15. The system of claim 11, wherein the one or more processors are configured to optimize the objective function subject to the one or more first constraints and the second constraint using linear programming.

16. The system of claim 11, wherein to optimize the objective function subject to the one or more first constraints and the second constraint the one or more processors are configured to solve for dwell time durations for a plurality of dwell positions, and wherein the optimization problem further includes a constraint on dwell time durations for neighboring dwell positions.

17. The system of claim 11, wherein the one or more processors are configured to:

determine a region around the PTV, wherein the optimization problem further includes a third constraint on radiation doses within the region around the PTV; and optimize the objective function subject to the one or more first constraints, the second constraint and the third constraint.

18. The system of claim 11, wherein the one or more processors are configured to:

identify, for each OAR region, a sub-region of the OAR region expected to have highest radiation doses in the OAR region; and optimize the objective function subject to the one or more first constraints applied to radiation doses within the sub-regions of the OAR regions.

19. The system of claim 11, wherein the one or more processors are configured to:

generate, using the patient specific data, a three-dimensional (3D) structure representing an anatomical region of the patient;

downsample the 3D structure; and optimize the objective function within the downsampled 3D structure.

20. A non-transitory computer-readable medium storing computer instructions, the computer instructions when executed by one or more processors cause the one or more processors to:

obtain patient specific data of a patient, the patient specific data including information of an anatomical region of the patient having a planning target volume (PTV) and one or more organ-at-risk (OAR) regions, and indications of a plurality of clinical goals;

determine, using the patient specific data, an optimization problem to solve for a single-fraction HDR monotherapy plan, the optimization problem including an objective function to be optimized subject to one or more first constraints on radiation doses within the one or more OAR regions and a second constraint on radiation doses within the PTV;

optimize the objective function subject to the one or more first constraints and the second constraint;

determine whether the single-fraction HDR monotherapy plan satisfies the one or more first constraints and the second constraint;

update a bound value of the second constraint based on whether the single-fraction HDR monotherapy plan satisfies the one or more first constraints and the second constraint; and optimize the objective function subject to the one or more first constraints and the second constraint with the updated bound value.

* * * * *